United States Patent
Cornacchia

(10) Patent No.: US 10,646,268 B2
(45) Date of Patent: *May 12, 2020

(54) ERGONOMIC ACTUATOR FOR ELECTROSURGICAL TOOL

(71) Applicant: BIPAD, INC., Point Lookout, NY (US)

(72) Inventor: Louis Cornacchia, Point Lookout, NY (US)

(73) Assignee: BIPAD, INC., Point Lookout, NY (US)

( * ) Notice: Subject to any disclaimer, the term of this patent is extended or adjusted under 35 U.S.C. 154(b) by 654 days.

This patent is subject to a terminal disclaimer.

(21) Appl. No.: 15/248,735

(22) Filed: Aug. 26, 2016

(65) Prior Publication Data

US 2018/0055558 A1 Mar. 1, 2018

(51) Int. Cl.
*A61B 18/14* (2006.01)
*A61B 18/00* (2006.01)

(52) U.S. Cl.
CPC ......... *A61B 18/1442* (2013.01); *A61B 2018/00589* (2013.01); *A61B 2018/00595* (2013.01);
(Continued)

(58) Field of Classification Search
CPC ........ A61B 18/1462; A61B 2017/0042; A61B 2017/00446; A61B 18/1442; A61B 18/1206; A61B 18/085
See application file for complete search history.

(56) References Cited

U.S. PATENT DOCUMENTS

| 2,176,479 A | 10/1939 | Willis |
| 4,370,980 A | 2/1983 | Lottick |

(Continued)

FOREIGN PATENT DOCUMENTS

| EP | 0834891 A2 | 4/1998 |
| EP | 1347705 B1 | 12/2005 |

(Continued)

OTHER PUBLICATIONS

International Search Report dated Aug. 25, 2015, in PCT/US2015/033429.

(Continued)

*Primary Examiner* — Jaymi E Della
*Assistant Examiner* — Rachel A. Vierra
(74) *Attorney, Agent, or Firm* — David M. Quinlan, P.C.

(57) ABSTRACT

An actuator assembly for selectively transmitting a heating current from a bipolar electrical generator to a surgical tool includes an actuating component with a connector for mounting the actuator assembly to the tool in a predetermined orientation. A lever arm mounted for rotation to the actuating component controls a switch that introduces current to tool electrodes when the switch is closed. A user holds the tool and the mounted actuator assembly in one hand and operates the switch with an ergonomic lever arm rotatably mounted to the actuating component. Different left- and right-hand versions of the lever arm can be used with the same actuator assembly, or the actuator assembly can accept a different lever arm configuration for use with either hand. In another version, the actuator assembly can include a guard for preventing inadvertent actuation of the switch during one-handed manipulation of the tool.

20 Claims, 15 Drawing Sheets

(52) U.S. Cl.
CPC ............... *A61B 2018/00601* (2013.01); *A61B 2018/1462* (2013.01)

(56) References Cited

U.S. PATENT DOCUMENTS

| | | | |
|---|---|---|---|
| 4,552,143 | A | 11/1985 | Lottick |
| 5,116,333 | A | 5/1992 | Beane |
| 5,197,964 | A | 3/1993 | Parins |
| 5,282,799 | A | 2/1994 | Rydell |
| 5,472,442 | A | 12/1995 | Klicek |
| 5,634,924 | A | 6/1997 | Turkel et al. |
| 5,860,975 | A | 1/1999 | Goble et al. |
| 5,891,140 | A | 4/1999 | Ginn et al. |
| 6,106,524 | A | 8/2000 | Eggers et al. |
| 6,235,027 | B1 | 5/2001 | Herzon |
| 6,551,312 | B2 | 4/2003 | Zhang et al. |
| 6,569,163 | B2 | 5/2003 | Hata et al. |
| 6,747,218 | B2 | 6/2004 | Huseman et al. |
| 7,534,243 | B1 | 5/2009 | Chin et al. |
| 7,578,815 | B2 | 8/2009 | Howell |
| 7,695,470 | B1 | 4/2010 | Stewart et al. |
| 7,803,152 | B2 | 9/2010 | Honda et al. |
| 8,075,559 | B2 | 12/2011 | Stewart et al. |
| 8,133,219 | B2 | 3/2012 | Sato |
| 8,317,784 | B2 | 11/2012 | Choe et al. |
| 8,479,969 | B2 | 7/2013 | Shelton, IV |
| 8,534,528 | B2 | 9/2013 | Shelton, IV |
| 8,558,880 | B2 | 10/2013 | Nambakam et al. |
| 8,568,400 | B2 | 10/2013 | Gilbert |
| 8,622,274 | B2 | 1/2014 | Yates et al. |
| 8,632,535 | B2 | 1/2014 | Shelton, IV et al. |
| 8,638,057 | B2 | 1/2014 | Goldberg et al. |
| 8,638,191 | B2 | 1/2014 | Hamel et al. |
| 8,652,120 | B2 | 2/2014 | Giordano et al. |
| 8,684,253 | B2 | 4/2014 | Giordano et al. |
| 8,747,400 | B2 | 6/2014 | Bigley et al. |
| 8,840,603 | B2 | 9/2014 | Shelton, IV et al. |
| 9,433,460 | B2 | 9/2016 | Cornacchia |
| 9,707,028 | B2 | 7/2017 | Batchelor et al. |
| 2002/0128646 | A1 | 9/2002 | Zhang et al. |
| 2004/0172011 | A1 | 9/2004 | Wang et al. |
| 2005/0267553 | A1 | 12/2005 | Staunton et al. |
| 2008/0140158 | A1 | 6/2008 | Hamel et al. |
| 2008/0319442 | A1 | 12/2008 | Unger et al. |
| 2009/0012519 | A1 | 1/2009 | Manrique et al. |
| 2009/0085718 | A1 | 4/2009 | Hamel et al. |
| 2009/0248019 | A1 | 10/2009 | Falkenstein et al. |
| 2009/0275940 | A1 | 11/2009 | Malackowski et al. |
| 2010/0087817 | A1 | 4/2010 | Sato |
| 2011/0077640 | A1 | 3/2011 | Rioux et al. |
| 2011/0121049 | A1 | 5/2011 | Malinouskas et al. |
| 2011/0125138 | A1 | 5/2011 | Malinouskas et al. |
| 2011/0251612 | A1 | 10/2011 | Faller et al. |
| 2012/0116391 | A1 | 5/2012 | Houser et al. |
| 2012/0123405 | A1 | 5/2012 | Moua et al. |
| 2012/0172873 | A1 | 7/2012 | Artale et al. |
| 2013/0041292 | A1 | 2/2013 | Cunningham |
| 2013/0310829 | A1 | 11/2013 | Cohen |
| 2014/0276800 | A1* | 9/2014 | Batchelor .......... A61B 18/1442 606/42 |
| 2014/0336634 | A1 | 11/2014 | Gomez |
| 2015/0265305 | A1* | 9/2015 | Stulen ............ A61B 17/320068 606/169 |
| 2015/0342667 | A1 | 12/2015 | Cornacchia |

FOREIGN PATENT DOCUMENTS

| | | |
|---|---|---|
| EP | 1596743 B1 | 4/2008 |
| EP | 2057955 A1 | 5/2009 |
| EP | 2324776 A2 | 5/2011 |
| EP | 2377476 A1 | 10/2011 |
| EP | 2377476 B1 | 3/2015 |
| FR | 2668918 | 11/1990 |
| JP | 10192295 | 7/1998 |
| JP | 2009222018 | 6/2009 |
| WO | 9829044 | 7/1998 |
| WO | 2006050410 A1 | 5/2006 |

OTHER PUBLICATIONS

Written Opinion dated Aug. 25, 2015, in PCT/US2015/033429.
European Search Report in EPO appln. No. 15798750.4, dated Jan. 2, 2018.
Examination Report No. 1, Australian appln. No. 2015266597, dated Feb. 21, 2019.
Office action in Chinese appln. No. 201580028967.3, dated Sep. 25, 2018 (with translation).
Response to Office action in Chinese appln. No. 201580028967.3, dated Mar. 27, 2019 (with translation).
Response to European Search Report in EPO appln. No. 15798750.4, dated Jul. 17, 2018.
Office action in Japanese appln. No. 2017-515040, dated Mar. 22, 2019 (with translation).
International Search Report and Written Opinion dated Feb. 5, 2020, in Appln. No. PCT/US2019/063550.

* cited by examiner

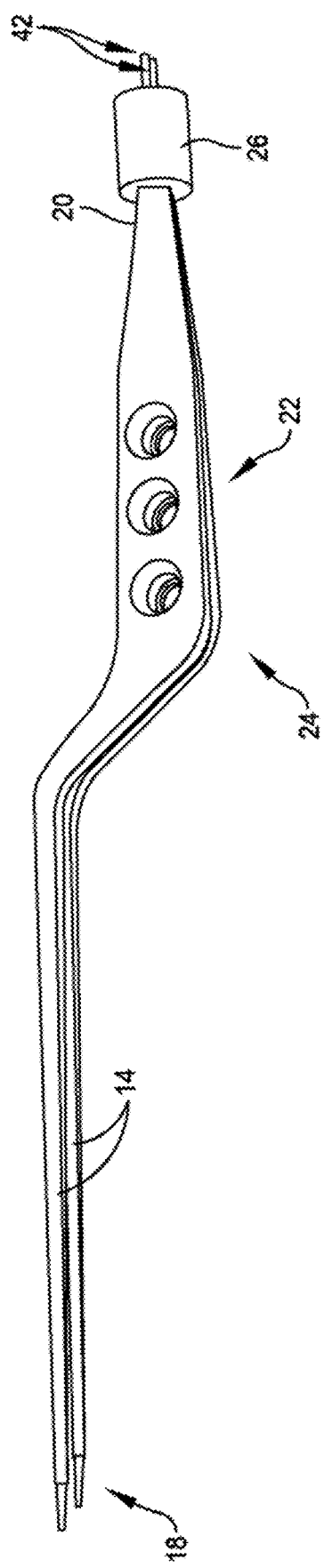
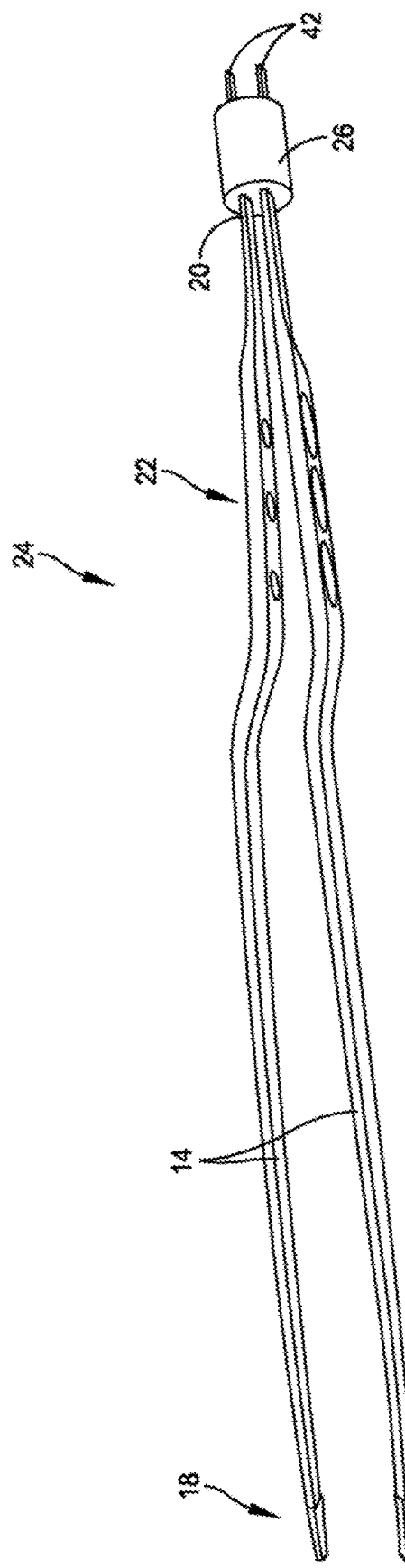
FIGURE 2a (PRIOR ART)
FIGURE 2b (PRIOR ART)

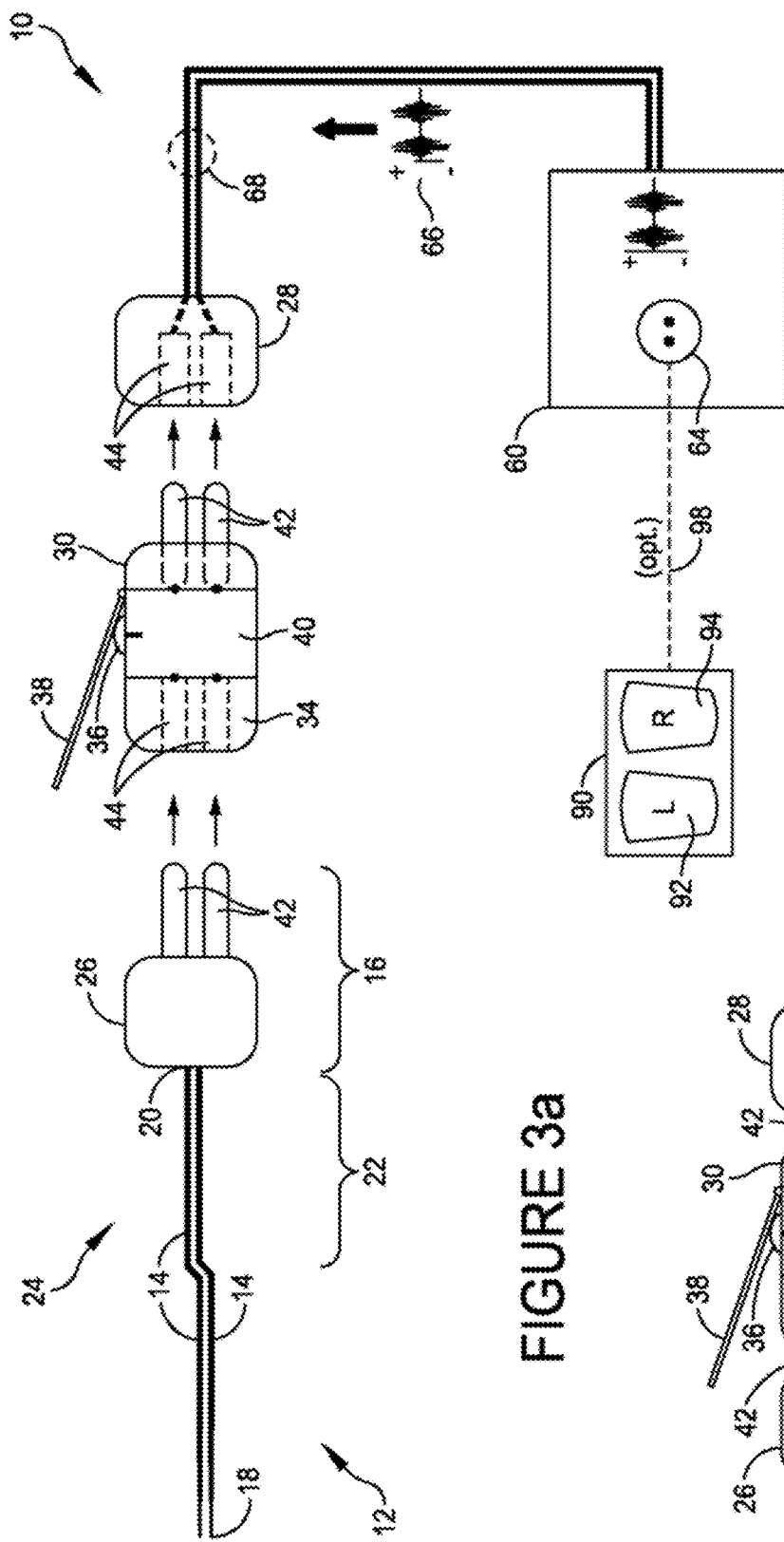
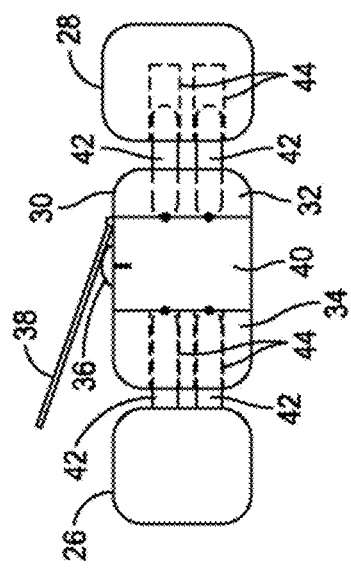
FIGURE 3a
FIGURE 3b

ERGONOMIC ACTUATOR FOR ELECTROSURGICAL TOOL

CROSS-REFERENCE TO RELATED APPLICATIONS

This application incorporates by reference the entire contents of U.S. patent application Ser. No. 14/726,490, filed on May 30, 2015, now U.S. Pat. No. 9,433,460, and U.S. provisional application No. 62/005,290, filed May 30, 2014.

BACKGROUND OF THE INVENTION

Bipolar electrosurgery, including bipolar electrocautery, is widely used to apply a heating current to a very localized volume of tissues in order to achieve hemostasis (cauterization, coagulation) or to dissect (cut) tissues, such as during neurosurgery. Typically, a bipolar generator resting near the operating table generates steady or intermittent voltages which are delivered through a power cord to a bipolar electrosurgical tool, such as a forceps. A foot pedal controller operated by the surgeon connects to the bipolar generator through a pedal control line separate from the power cord delivering the heating current to the forceps. Unfortunately, the location of the pedal controller is often not aligned with the surgeon's foot, requiring that the surgeon grope for the pedal or contort his or her body position in order to depress the correct pedal, posing significant risk and delay to the surgery in progress.

One solution is to have a surgeon's assistant move the pedal controller to a position which is close to the surgeon's foot. But this, again, adds delay to the surgery. Further, if the surgeon moves to another standing position, the location of the pedal controller may no longer be reliably known by the surgeon. Additionally, the pedal control line is an additional cable in an operating room already full of instruments and cables, and may thereby create clutter and a risk of falling.

BRIEF SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is disclosed a system for selectively actuating a heating current conductible from a bipolar generator to a surgical tool and which may comprise an actuator assembly having an output receptacle, an input plug, and an actuating component. The output receptacle may be configured to receive a complementary tool plug of the surgical tool. The input plug may be configured for mating with a generator receptacle receivable of the heating current from the bipolar generator. The actuating component may have at least one of a switch and a lever arm and may be configured to communicate with the bipolar generator for selectively actuating the heating current to flow from the input plug to the output receptacle upon engagement of the switch or the lever arm.

In another embodiment, there is disclosed a system for selectively actuating a heating current conductible from a bipolar generator to a surgical tool, and which may comprise two elongated conducting members extending from a base end of the surgical tool to a heating end of the surgical tool. The base end may be configured to receive the heating current from the bipolar generator through a power cord. The heating end may effectuate at least one of the following modes of operation of the surgical tool: cutting or coagulation. An actuator assembly may interpose one of the power cord and at least one of the elongated conducting members within a base portion of the surgical tool nearer the base end. The interposition may result in a generator terminal conductive to the bipolar generator and a tip terminal conductive to the heating end. The actuator assembly may comprise an actuating component having at least one of a switch and a lever arm and being configured to communicate with the bipolar generator to selectively actuate the heating current to flow from the generator terminal to the tip terminal upon engagement of the switch or the lever arm.

In yet another embodiment, there is disclosed a method for selectively actuating a heating current conductible from a bipolar generator to an electrosurgical forceps, and which may comprise interposing an actuating component along an available current path extending between a handle of the forceps and the bipolar generator. The bipolar generator may be capable of delivering the heating current for effectuating at a heating end of the forceps at least one of a cutting mode and a coagulation mode. The method may further comprise disposing on the actuating component at least one of a switch and a lever arm. The method may further comprise engaging the switch or the lever arm by one of a surgeon and a surgeon's assistant, the switch or the lever arm being configured for human operation by one of a hand and an upper body. The method may further comprise the actuating component communicating with the bipolar generator to selectively actuate the heating current to flow to the heating end of the forceps upon engagement of the switch or the lever arm.

In a still further embodiment an actuator assembly is mounted directly to an electrosurgical tool and includes an ergonomic actuating lever arm that enables the surgeon to hold the tool in one hand to maneuver it into position for effecting a surgical procedure and to use the same hand to actuate the tool at a desired time. In one configuration the actuator assembly has right- and left-hand versions. In another configuration the same actuator assembly can be adapted for right- or left-hand operation. In another aspect of this embodiment, the actuator assembly includes a guard for preventing inadvertent actuation of the tool by the surgeon's hand as he or she maneuvers the tool into position.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIGS. 2a-2b (prior art) illustrate an embodiment of electrosurgical forceps connected by a tool plug.

FIGS. 3a-3b illustrate an exemplary embodiment of an in-line actuator assembly for a bipolar electrosurgical actuating system and method, in accordance with an embodiment of the present disclosure.

FIGS. Sa-Sb illustrate an exemplary embodiment of an in-line actuator assembly separated by a jumper cord for a bipolar electrosurgical actuating system and method.

Figure 6:
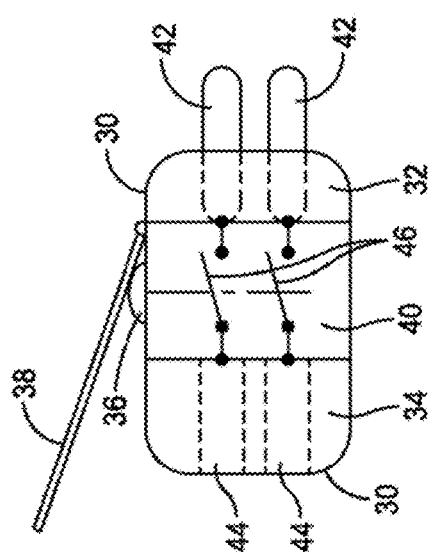

FIG. 6 illustrates an exemplary embodiment of a hard electrical switch for facilitating an actuating component for a bipolar electrosurgical actuating system and method.

Figure 7:
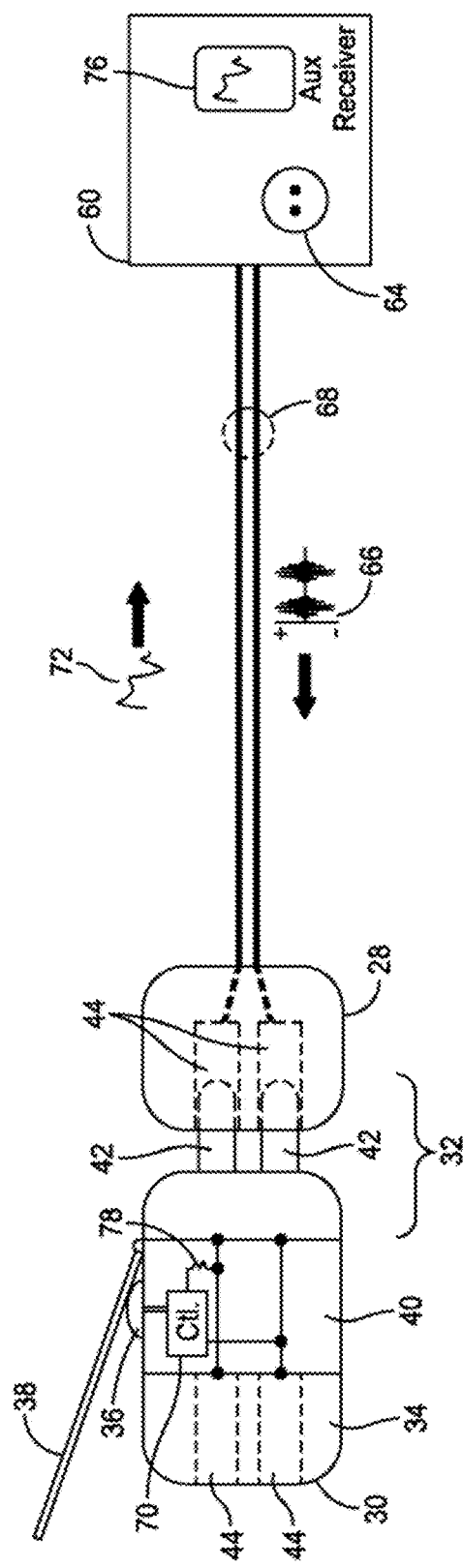

FIG. 7 illustrates an exemplary embodiment of a control signaling component coupled to the input plug for facilitating an actuating component for a bipolar electrosurgical actuating system and method.

Figure 8:
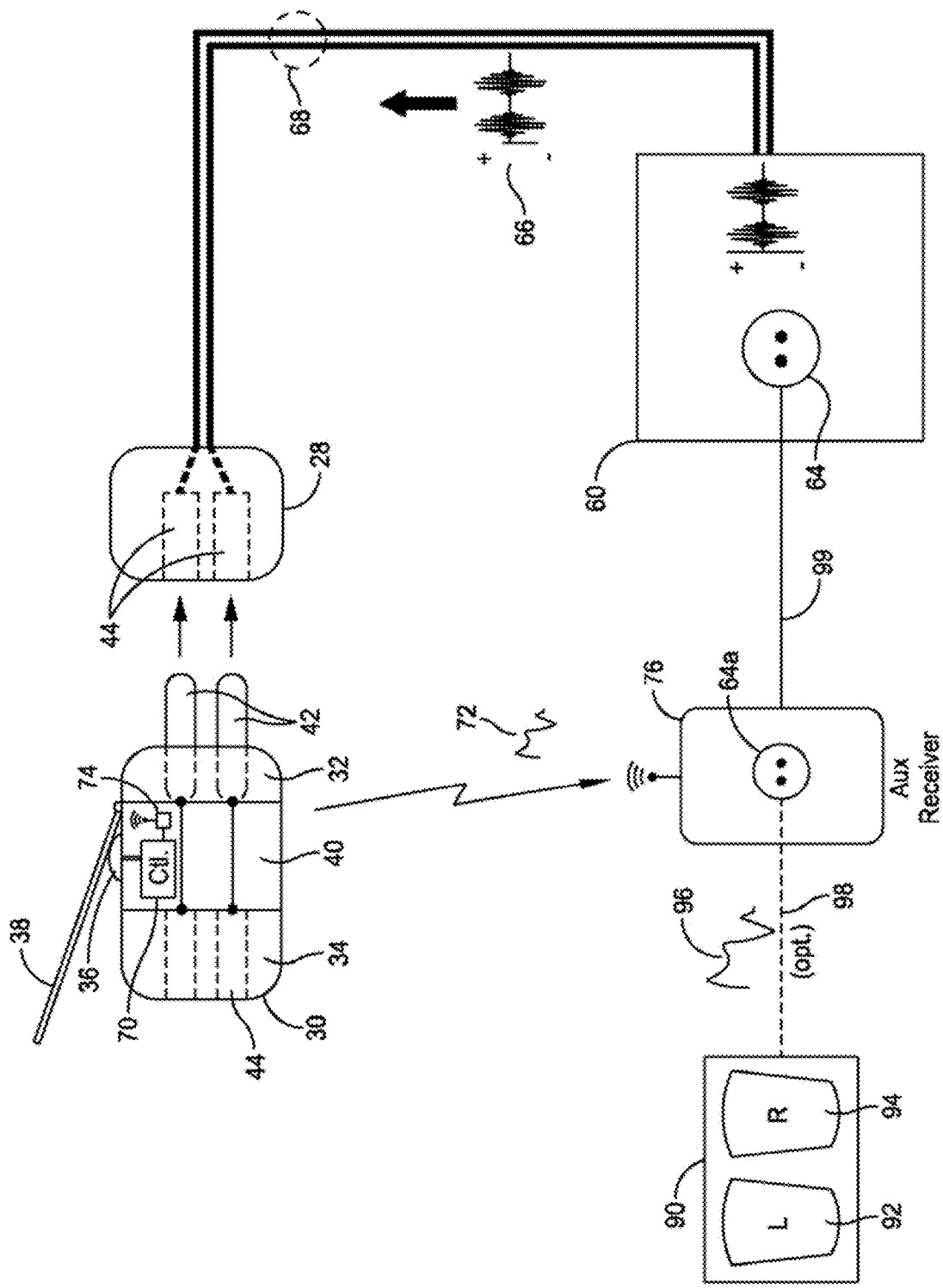

FIG. 8 illustrates an exemplary embodiment of a control signaling transmitted to an auxiliary receiver for facilitating an actuating component for a bipolar electrosurgical actuating system and method.

Figure 9:
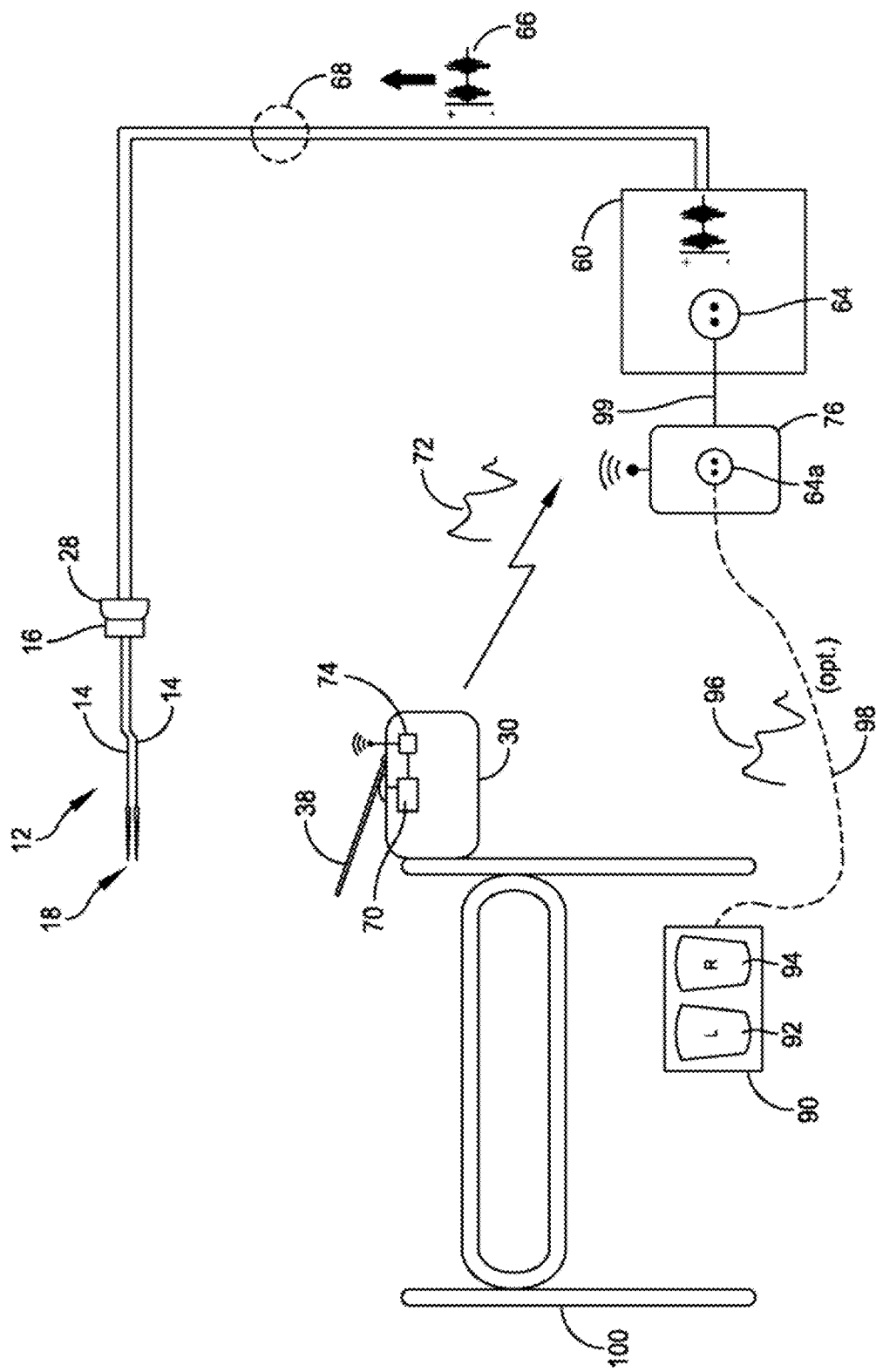

FIG. 9 illustrates an exemplary embodiment of using the actuator assembly as a remote control for a bipolar electrosurgical actuating system and method.

Figure 10:
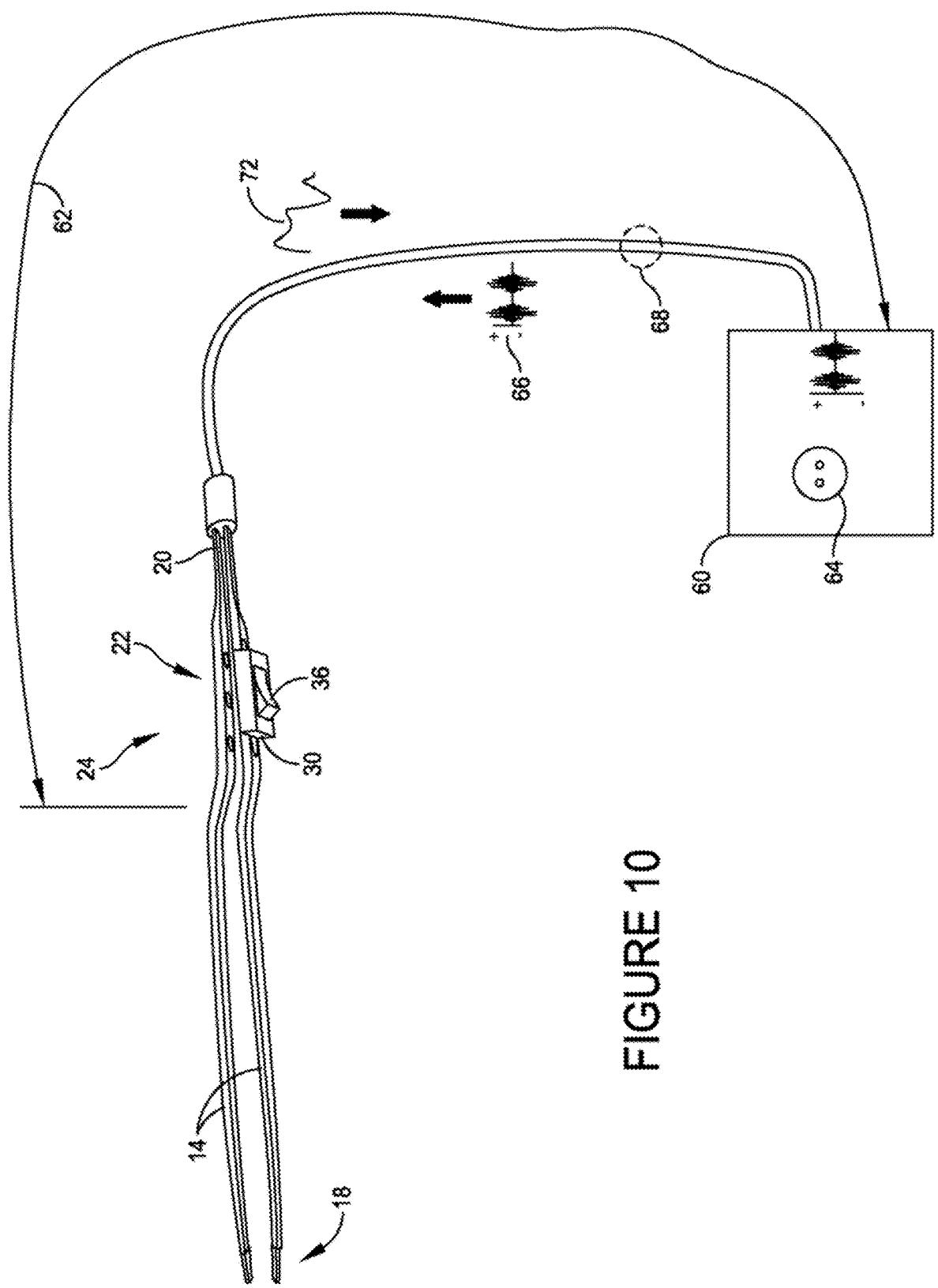

FIG. 10 illustrates an exemplary embodiment of an actuator assembly integrated into a forceps for a bipolar electrosurgical actuating system and method.

Figure 11:
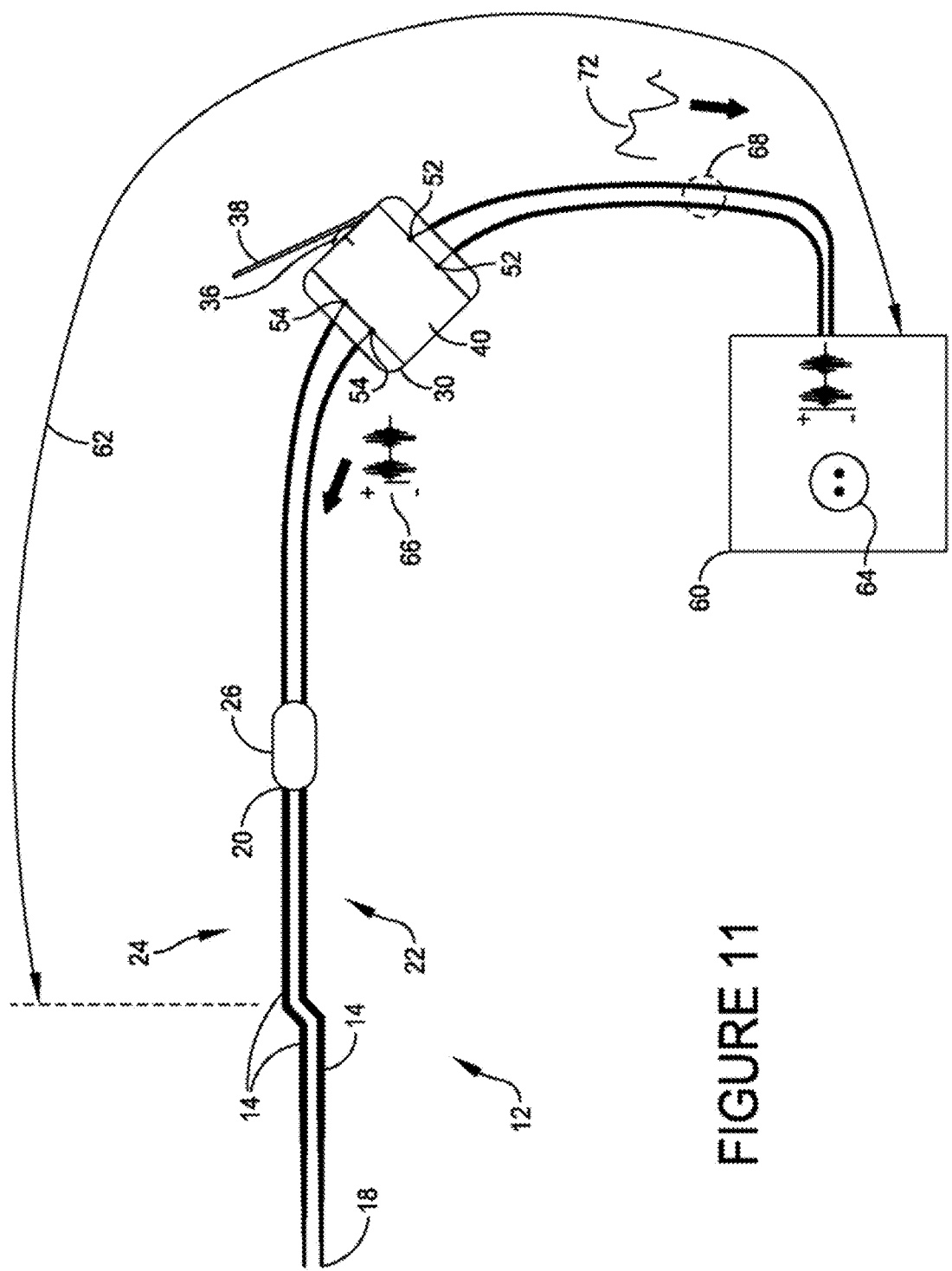

FIG. 11 illustrates an exemplary embodiment of an actuator assembly integrated into a power cord for a bipolar electrosurgical actuating system and method.

Figure 12:
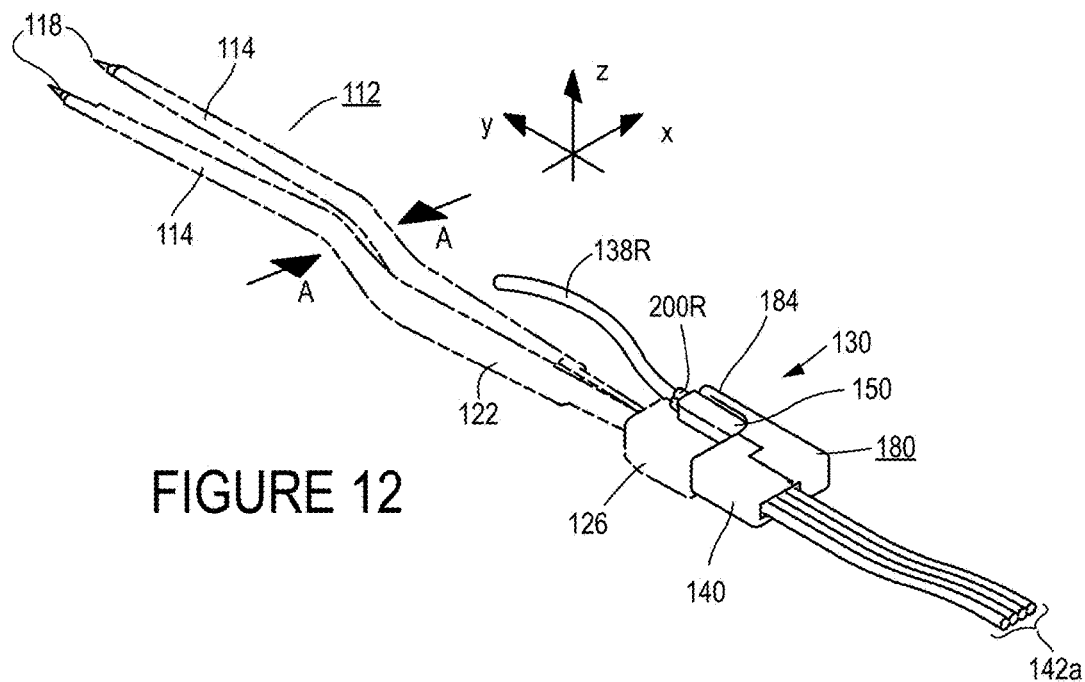

FIG. 12 is an isometric view of an exemplary embodiment of an actuator assembly with an ergonomic control arm configured for right-handed operation of an electrosurgical forceps tool (shown in phantom lines in the figures).

Figure 13:
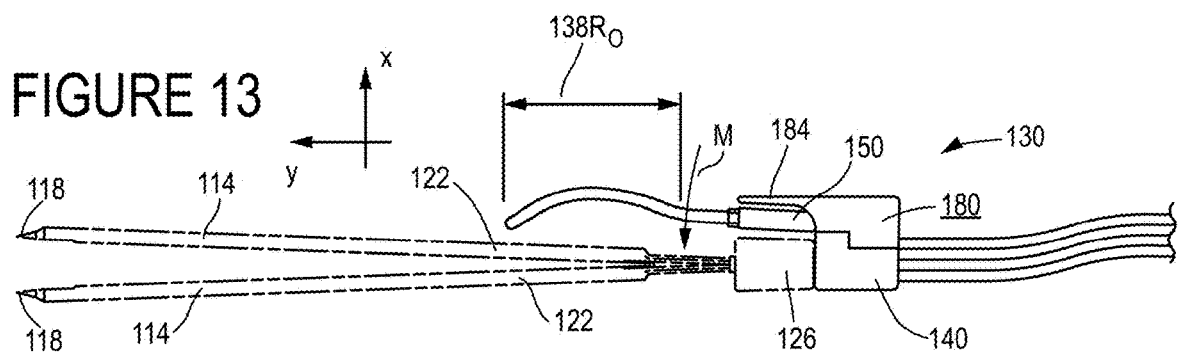

FIG. 13 is a top view of the actuator assembly shown in FIG. 12.

Figure 14:
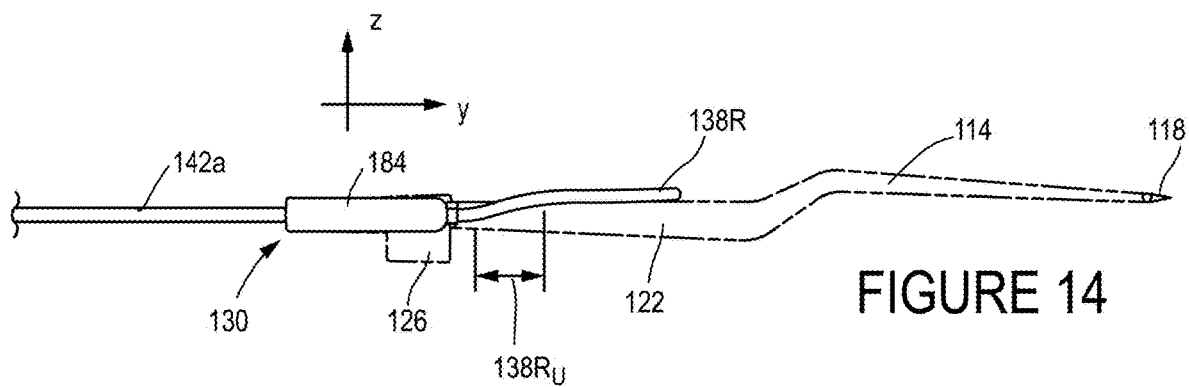

FIG. 14 is a right side view of the actuator assembly shown in FIG. 12.

Figure 15:
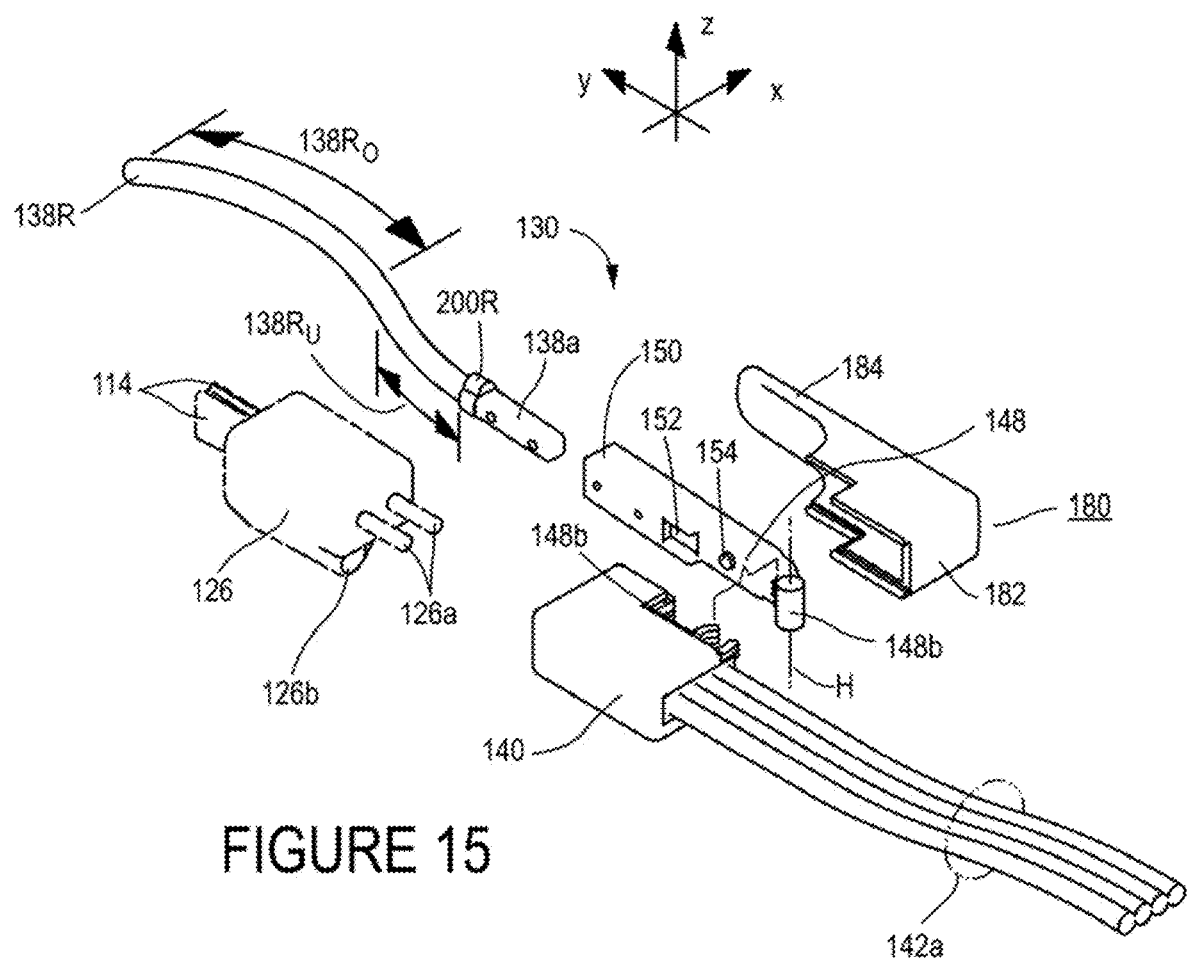

FIG. 15 is an exploded view of the actuator assembly shown in FIG. 12.

Figure 16:
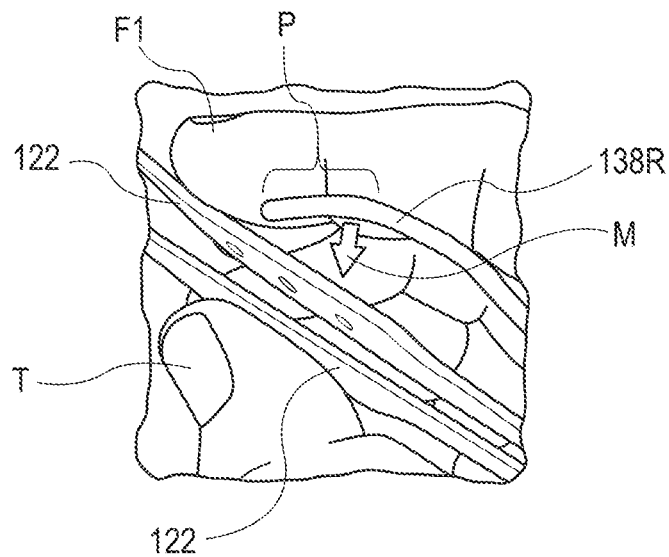

FIG. 16 depicts one manner of operating the forceps tool with the actuator assembly shown in FIGS. 12-15 attached.

Figure 17:
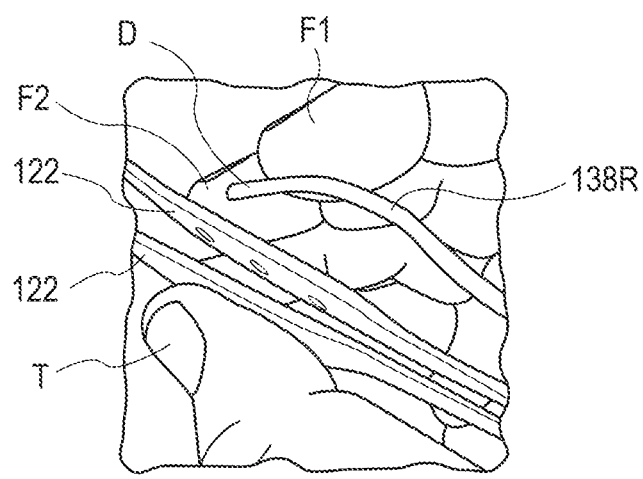

FIG. 17 depicts an alternate manner of operating the forceps tool with the same actuator assembly.

Figure 18:
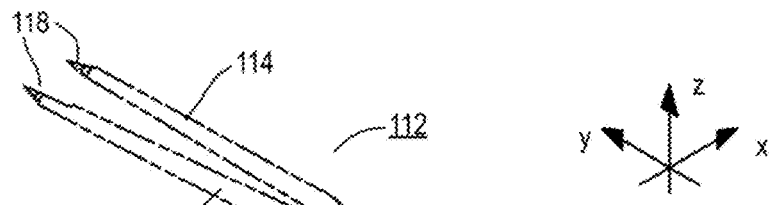

FIG. 18 is an isometric view of an exemplary embodiment of an actuator assembly with an ergonomic control arm configured for left-handed operation of an electrosurgical forceps tool.

Figure 19:
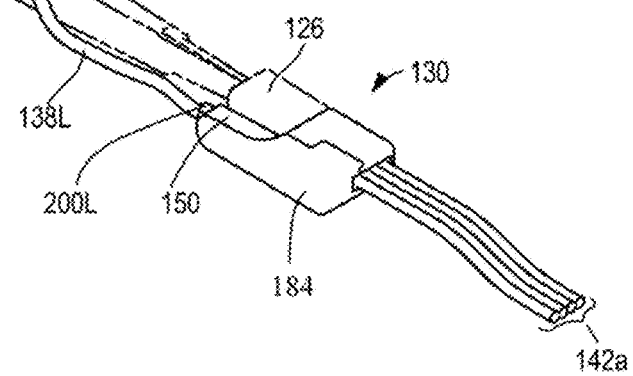

FIG. 19 is a top view of the actuator assembly shown in FIG. 18.

Figure 20:
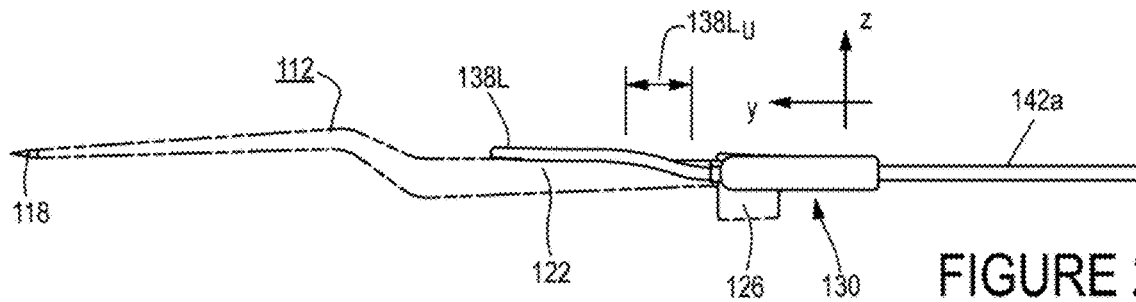

FIG. 20 is a left side view of the actuator assembly shown in FIG. 18.

Figure 21:
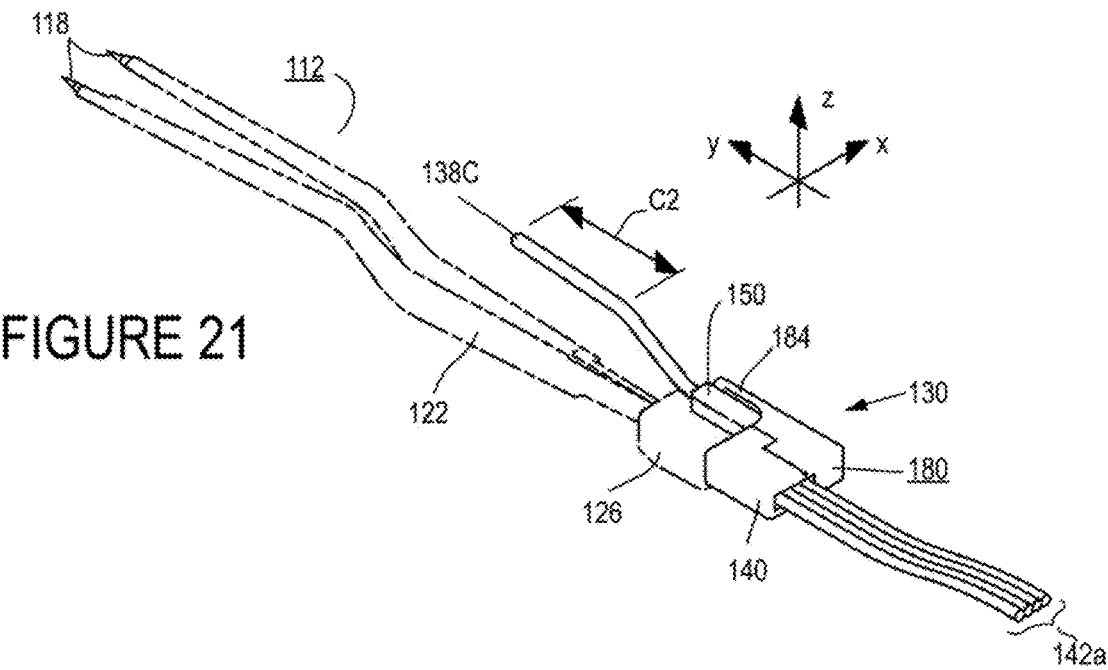

FIG. 21 is an isometric view of an exemplary embodiment of an actuator assembly with an ergonomic control arm capable of being mounted for right-handed or left-handed operation of an electrosurgical forceps tool.

Figure 22:
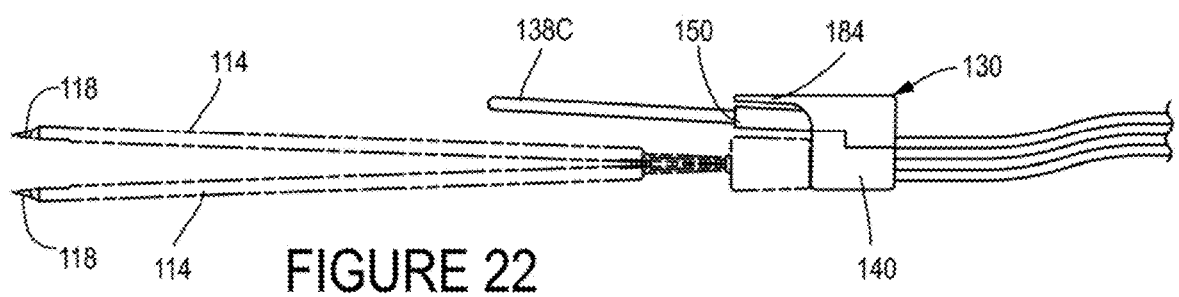

FIG. 22 is a top view of the actuator assembly shown in FIG. 21.

Figure 23:
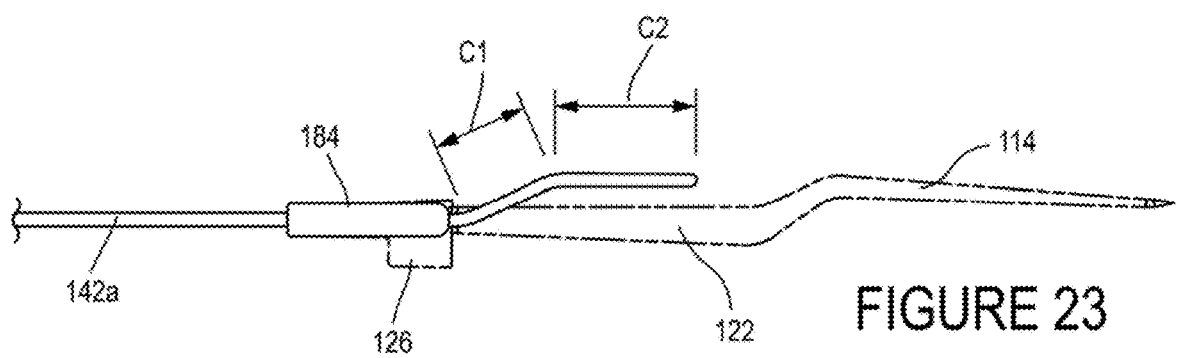

FIG. 23 is a right side view of the actuator assembly shown in FIG. 21.

DETAILED DESCRIPTION OF EMBODIMENTS OF THE INVENTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense. The detailed description that follows is intended to provide specific examples of particular embodiments illustrating various ways of implementing the claimed subject matter. It is written to take into account the level of knowledge of one of ordinary skill in the art to which the claimed subject matter pertains. Accordingly, certain details may be omitted as being unnecessary for enabling such a person to realize the embodiments described herein. In addition, spatially relative terms such as "upward," "downward," "top," "bottom," "right," "left," "under," "over," "proximal," "distal," etc., may be used herein for convenience, but they in no way limit the structure or procedure described, unless the context indicates otherwise. Similar considerations apply to the term "about," which is sometimes used herein to indicate that the nominal value of a parameter can vary a certain amount as long as it produces the intended effect or result.

In addition, terms used throughout are meant to have the ordinary and customary meaning that would be ascribed to them by one of ordinary skill in the art. However, some of the terms used in the description herein will be explicitly defined and that definition is meant to apply throughout. For example, the term "substantially" is sometimes used to indicate a degree of similarity of one item, such as a property, structural feature, or parameter, to another. This means that the items are sufficiently similar in value to achieve the purpose ascribed to them in the context of the description accompanying the use of the term. Exact equivalence of many items discussed herein is not possible because of factors such as engineering tolerances and normal variations in operating conditions, but such deviations from an exact identity still fall within the meaning herein of being "substantially" the same. Likewise, omission of the term "substantially" when equating two such items does not imply that they are identical unless the context suggests otherwise.

When elements are referred to as being "connected" or "coupled," the elements can be directly connected or coupled together or one or more intervening elements may also be present. In contrast, when elements are referred to as being "directly connected" or "directly coupled," there are no intervening elements present.

Figure 1:
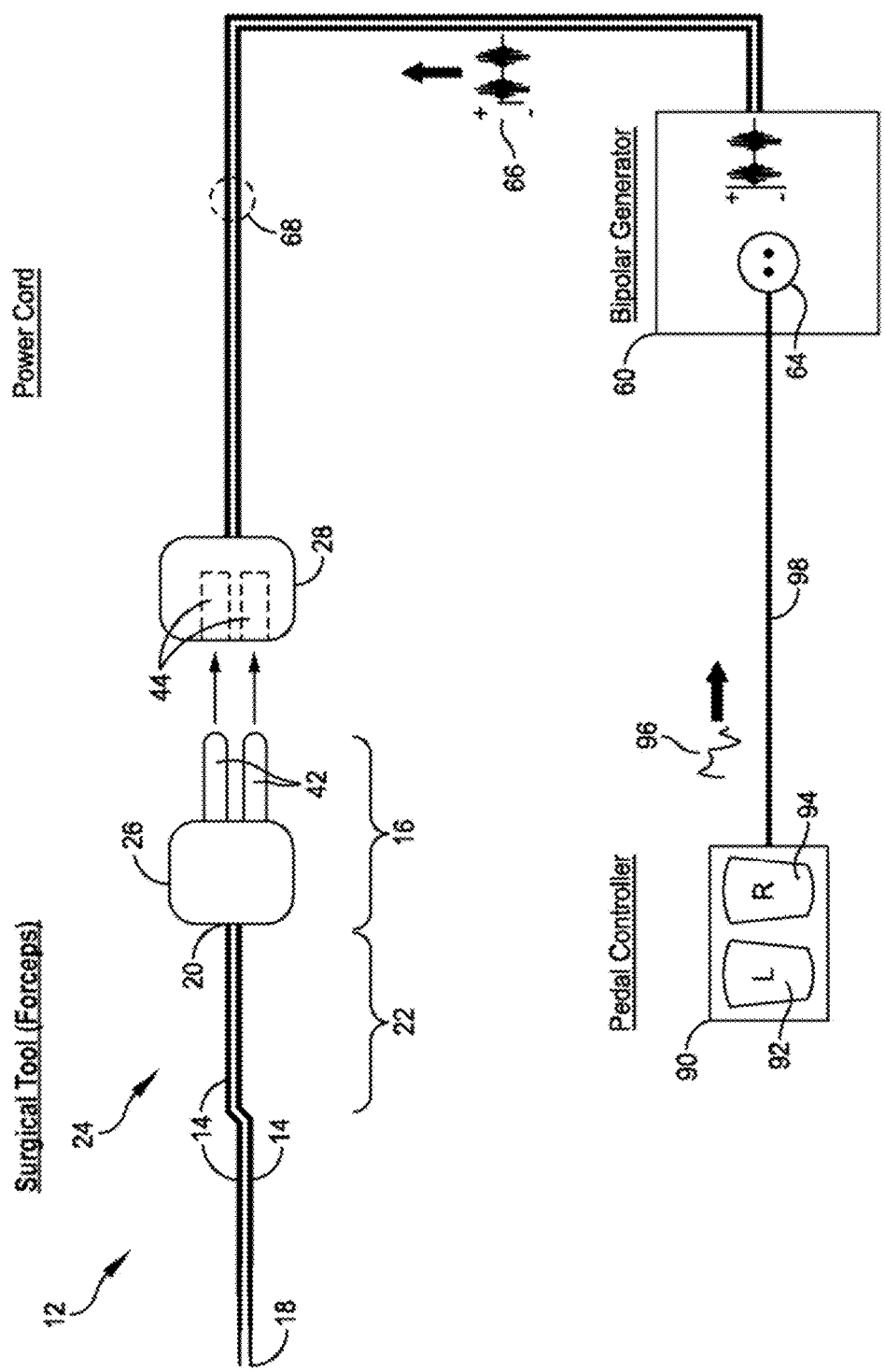
FIG. 1 (prior art) illustrates an embodiment of foot pedals used to initiate the flow of a heating current to electrosurgical forceps.

FIGS. 1 and 2a-2b illustrate a prior art system where pedal controller 90 may actuate bipolar generator 60 by means of pedal signaling 96 directed along pedal control line 98 and into control input 64. Left pedal 92 may be depressed to actuate a cutting mode for forceps 12, while right pedal 94 may be depressed to actuate a coagulation mode. In response to signals on pedal control line 98, a heating current 66 may be dispatched from bipolar generator 60 onto power cord 68 which may terminate in generator receptacle 28 having sockets 44. A power connector (not shown) on bipolar generator 60 may output the heating current 66 into a removably connectable power cord 68. The voltage waveform of heating current 66 may be intermittent for coagulation mode, as shown in FIG. 1, or may be continuous for cutting mode. Surgical tool (forceps) 12 may receive the heating current 66 through prongs 42 of tool plug 16 plugged into generator receptacle 28.

Continuing with FIGS. 1 and 2a-2b, two elongated blades 14 may be coated with an insulator or various insulation materials on all parts extending from base end 20 to heating end 18 in order to avoid a short circuit. However, the blades may be bare on the inside tips near heating end 18 for grabbing tissues to be cauterized or dissected by the passage of heating current 66. Heating current 66 may be an alternating current and have a frequency ranging from approximately 200 kHz to approximately 4.0 MHz. A handle 22 may be held by a surgeon and may allow for articulation of blades 14. Blades 14 may be insulatively bound together by insulator 26 and may allow for articulation of blades 14. Insulator 26 may also retain prongs 42 of tool plug 16. Base portion 24 may refer to the portion of the tool 12 closest to tool plug 26 and which is not involved in surgical effect, and may be approximately concurrent with handle 22.

Now referring to FIGS. 3a-3b, 4a-4b, 5a-5b, and 6-8, in various embodiments, a bipolar electrosurgical actuating system 10 may comprise an actuator assembly 30 having an output receptacle 34 with sockets 44, an input plug 32 with prongs 42, and an actuating component 40 arranged to pass a heating current 66 from prongs 42 to sockets 44. Actuator assembly 30 may be interposed in-line between a tool plug 16 of surgical tool (forceps) 12 and a generator receptacle 28 complementary to tool plug 16, as shown in FIG. 3b. The connector type chosen for output receptacle 34 and input plug 32 may be selected to match the size, style, and gender of the connector used by surgical tools 12 of different manufacturers. Actuating component 40 may include a switch 36 and a lever arm 38 and may be configured to communicate with bipolar generator 60 for selectively actuating the heating current 66 to flow from input plug 32 to output receptacle 34 upon engagement of the switch 36 or the lever arm 38. Alternately, actuating component 40 may include only a switch 36 or only a lever arm 38. Various means known in the art may facilitate selective actuation of bipolar generator 60 and which are described below for FIGS. 6-8.

Continuing, in various embodiments, heating current 66 may pass through power cord 68 to generator receptacle 28, through actuator assembly 30, and into forceps 12 at tool plug 16. Heating current 66 may then conduct through insulator 26 to base end 20 of blades 14 for effectuating at least one of a cutting mode and a coagulation mode at heating end 18. Base portion 24 may refer to the portion of the forceps 12 closest to tool plug 16 and which is not involved in surgical effect, and may be approximately concurrent with handle 22. Generalizing, surgical tool 12 may include two elongated conducting members (blades 14) terminating in a heating end 18. Alternatives to a forceps may include a hemostat, a scissors, a clamp, a clip, a scalpel, a hook, and a loop. Alternatives to the prong 42 and socket 44 connectors may include a wire terminal, a bayonet twist mount, a flush mount with screws, locking pins with a release, a snap, and a clamp. Alternatively, the tool plug 16 and input plug 32 may be configured as female connectors and the generator receptacle and output receptacle may be configured as male connectors. In another embodiment, not shown, assembly 30 may include a jumper cord (not shown) interposed between actuating component 40 and input plug 32, where generator receptacle 28 may be a power connector (not shown) mounted on the bipolar generator and outputting heating current 66 into an actuator assembly that includes the power cord feature. In this case, input plug 32 is chosen to mate with the power connector at bipolar generator 60.

Referring still to FIGS. 3a-3b, 4a-4b, 5a-5b, and 6-8, in various embodiments, pedal controller 90 may optionally be connected to bipolar generator 60 by pedal control line 98 for offering an additional method of selectively actuating bipolar generator 60. Left pedal 92 and right pedal 94 may be depressed to actuate a cutting mode or a coagulation mode, respectively. In an embodiment, selective actuation of bipolar generator 60 may be accomplished by a hard electrical switch 46 included in actuating component 40 and engaged by switch 36 for directly conducting the heating current 66 from input plug 32 to output receptacle 34 (FIG. 6). In another embodiment, selective actuation of bipolar generator 60 may be accomplished by a control circuit 70 included in actuating component 40 and generating a control signaling 72 conductively or inductively coupled by signaling tap 78 to input plug 32 for communicating with bipolar generator 60 for selectively actuating heating current 66 (FIG. 7). In yet another embodiment, selective actuation of bipolar generator 60 may be accomplished by an actuator transmitter 74 included in the actuating component 40, where a control signaling 72 may be wirelessly transmitted to and receivable by the bipolar generator 60 via auxiliary receiver 76 (FIG. 8). Additional description for FIGS. 6-8 is provided below.

Figure 4A:
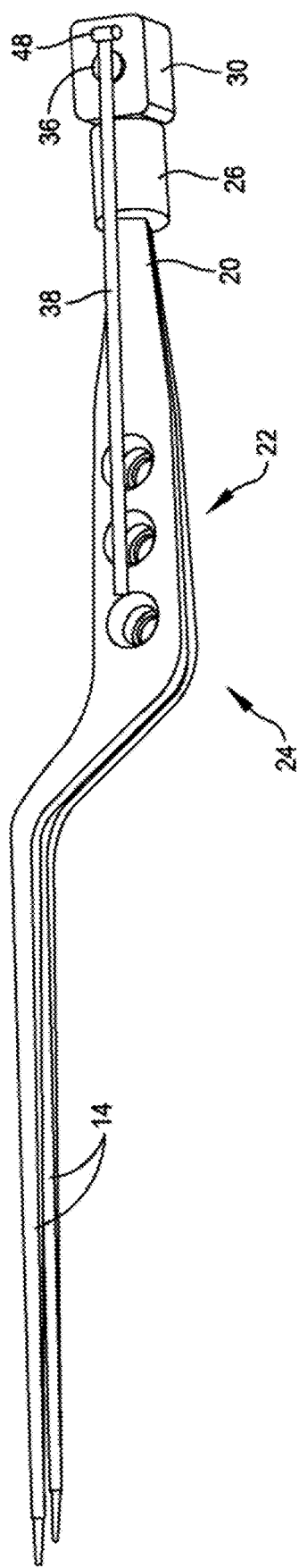
FIGS. 4a-4b illustrate an exemplary embodiment of an actuator assembly mounted to a forceps for a bipolar electrosurgical actuating system and method.
Figure 4B:
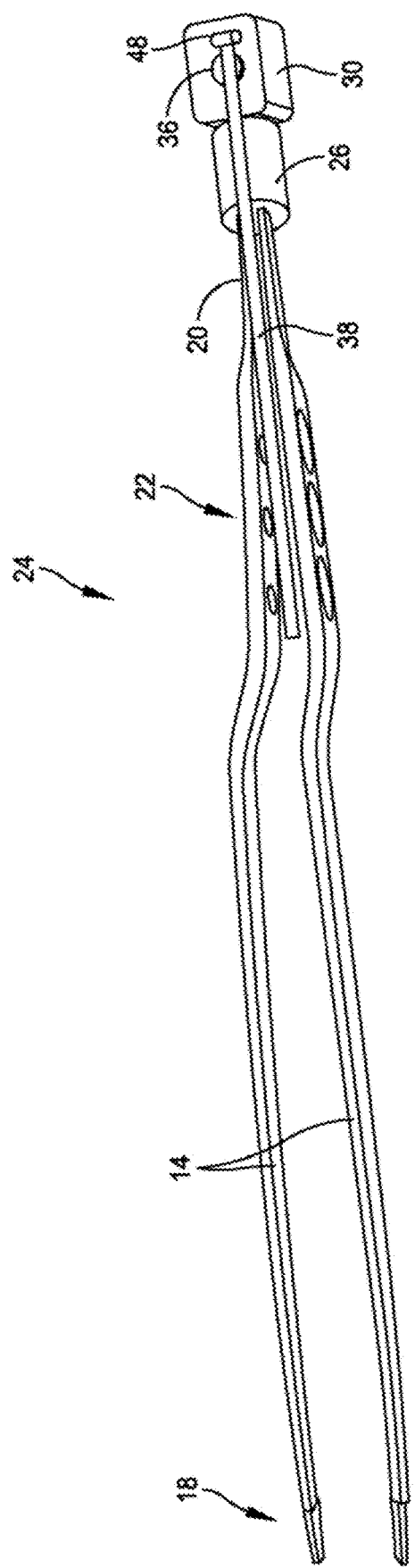

Continuing with FIGS. 3a-3b, 4a-4b, 5a-5b, and 6-8, in various embodiments, lever arm 38 may be hingedly moveable to engage switch 36 for selectively actuating the heating current 66. For example, one end of lever arm 38 may be hinged at 48 and configured to depress a momentary push button switch 36 when lever arm 38 is moved downward and toward assembly 30. Alternately, lever arm 38 may engage a rocker switch 36 (not shown) during a sideways movement parallel to the surface of assembly 30 and thereby actuate heating current 66. Referring to FIGS. 4a-4b, in an embodiment, lever arm 38 may extend over handle 22 along the sides of forceps 12 or the top or bottom of forceps 12, providing a convenient means for actuating heating current 66 using the same or opposite hand as the hand holding forceps 12. Lever arm 38 may be configured for operation by a human hand such that it conforms to the shape of the hand and its available range of motion to allow for a subtle and fault-free engagement without interfering with the articulation of forceps 12.

Still with FIGS. 3a-3b, 4a-4b, 5a-5b, and 6-8, in various embodiments, lever arm 38 may include a lever switch mechanism (not shown) for selectively actuating the heating current 66 in response to a displacement of the lever arm 38 by at least one of the following means: mechanical actuation, electrical resistance, piezoelectric pressure, electrostatic sensing. The displacement may be an angular pivoting, a pistoning of the lever shaft, a rotation the shaft, a flexing, or some other movement. The lever switch mechanism may eliminate a need for switch 36, or may provide additional control features in addition to those provided by switch 36. For example, lever arm 38 may be a rod extending from a piezoelectric "joystick" base (lever switch mechanism). Switch 36 may be configured as at least one of a push button, a slide switch, a rotating shaft, a joystick, an electrostatic sensor, a piezoelectric sensor, a temperature switch, a rocker switch, a momentary switch, and a voice-activated switch. Switch 36 may be used alone or in combination with lever arm 38. Advantageously, having a flexible means for interposing a switch 36 and/or lever arm 38 in-line with power cord 68 may provide a visible and/or reliably known location for selectively actuating heating current 66.

Figure 5A:
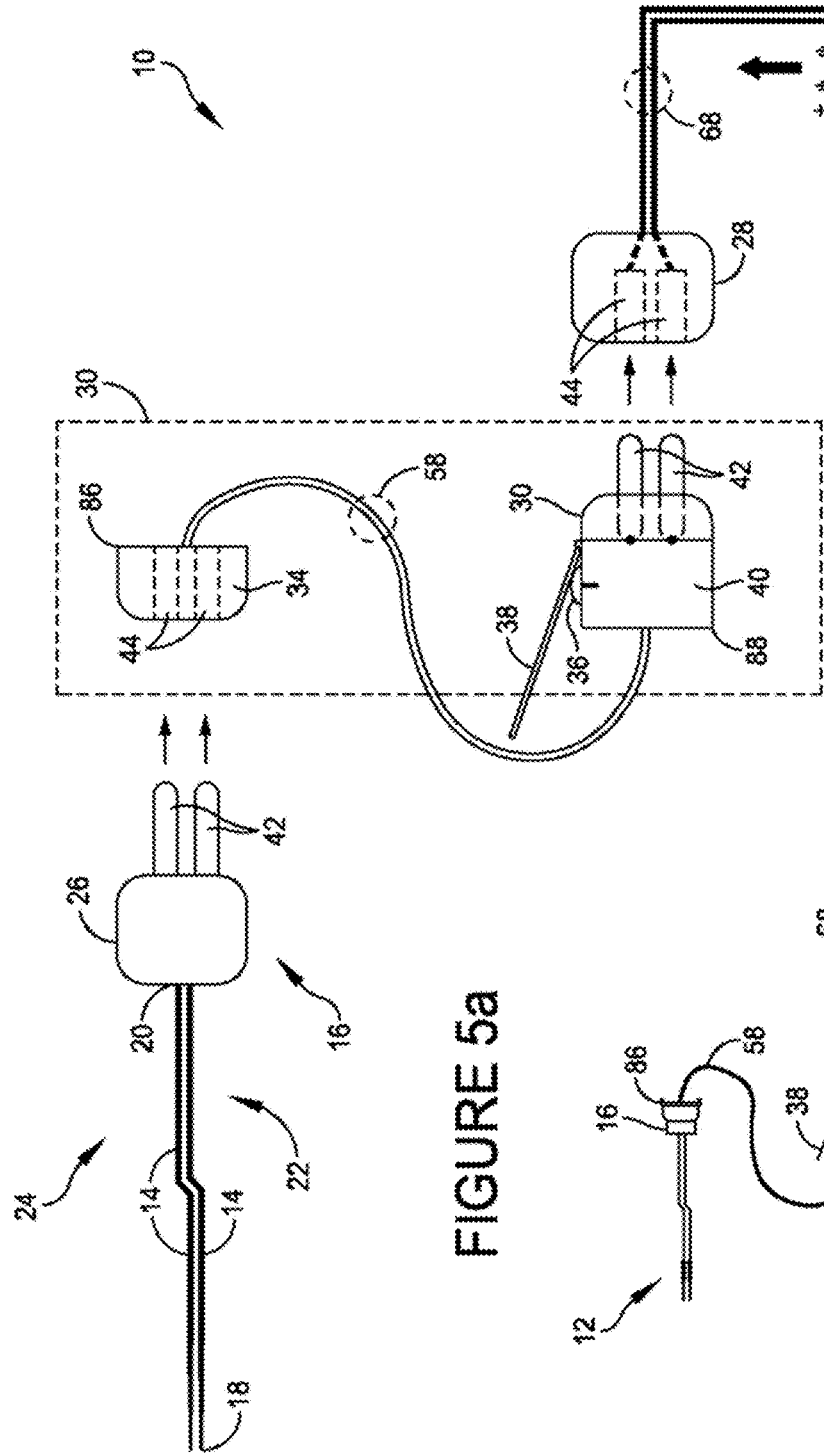
Figure 5B:
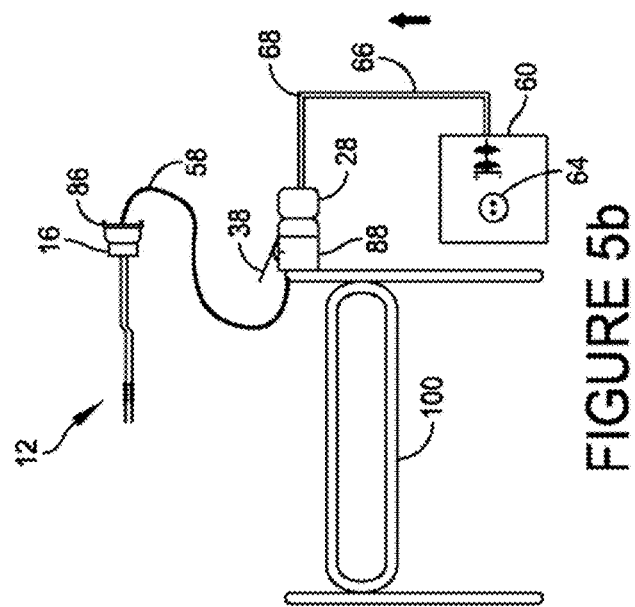

Referring now to FIGS. 5a-5b, in an embodiment, a jumper cord 58 may connect a tool portion 86 of actuator assembly 30 to a generator portion 88 of actuator assembly 30, the tool portion 86 containing output receptacle 34 and connecting to tool plug 16, the generator portion 88 containing input plug 32 and actuating component 40 and connecting to generator receptacle 28. In various embodiments, jumper cord 58 may separate and provide conduction between input plug 32 and output receptacle 34 for mounting the actuating component 40 to an operating table 100. For example, lever arm 38, when positioned at operating table 100, may be engaged by a human hand or hip. Alternatively, jumper cord 58 may enable the actuating component 40 to be held by a human hand, held actuatably in a human mouth, mounted to a positioning arm, mounted actuatably to a human upper body, or mounted to another piece of operating room equipment. In other embodiments, actuating component 40 may be interposed anywhere along an available current path (FIG. 10) concurrent with power cord 68 and extending from handle 22 of a surgical tool 12 to bipolar generator 60. For example, in an embodiment not shown, assembly 30 may include jumper cord 58 for separating and providing conduction between actuating component 40 and input plug 32, where generator receptacle 28 may be a power connector (not shown) mounted on the bipolar generator and outputting heating current 66 into an actuator assembly that includes the power cord feature. In this case, generator receptacle 28 may not be complementary to tool plug 16. Advantageously, providing an in-line method for selectively actuating heating current 66 may allow actuating component 40 to be flexibly positioned for reliable access by some part of a human upper body, thereby removing the limitations and uncertainty of a pedal controller 90.

Referring now to FIG. 6, in various embodiments, selective actuation of bipolar generator 60 may be accomplished by hard electrical switches 46 closing a circuit between input plug 32 and output receptacle 34 for each respective conductor. Hard electrical switch 46 may be a single-pole-single-throw type that may be mechanically or electrically engaged by switch 36. Alternatively, one hard electrical switch 46 may close the circuit of one of two bipolar conducting paths, the other circuit being continually closed. In an embodiment, a heating current 66 may be available at generator receptacle 28 at a desired preset condition, and engagement of hard electrical switch 46 may close the circuit actuating bipolar generator 60 to conduct heating current 66 to surgical tool 12. In this case, the engagement of hard electrical switch 46 may constitute a communication with and an actuation of bipolar generator 60. For example, a surgeon may depress left pedal 92 for effectuating a cutting mode, and then engage switch 36 to pass the heating current 66 to a forceps 12 at the precise moment required. Advantageously, a precision cut may be engaged by a switch 36 or lever arm 38 located at or above a waist level and having a finer movement than a large, heavy foot pedal not visible to the surgeon.

Continuing with FIG. 6, in an embodiment not shown, selective actuation of bipolar generator 60 may be accomplished by a hard electrical switch closing a circuit between two auxiliary wires (not shown) incorporated into power cord 68 for tripping a relay (not shown) actuating the heating current 66. The relay may be internal to generator 60 or may be included in an auxiliary receiver that generates a pedal signaling 96 for control input 64. A continuous pass-through connection may exist between input plug 32 and output receptacle 34.

Referring to FIG. 7, in an embodiment, selective actuation of bipolar generator 60 may be accomplished by a control circuit 70 included in actuating component 40 and generating a control signaling 72 corresponding to an engagement of switch 36 or lever arm 38 and conductively or inductively coupled by signaling tap 78 to input plug 32 for communicating with bipolar generator 60 to selectively actuate heating current 66. Bipolar generator 60 may include auxiliary receiver 76 (which is illustrated internal to bipolar generator 60) for decoding control signaling 72. Receiver 76 may decode control signaling 72 into a control format similar to that of pedal signaling 96 conventionally received by pedal controller 90 for effectuating one of a cutting mode or a coagulation mode. Additionally, control signaling may effectuate an OFF mode where there is no current flow. A closed circuit may exist between receptacle 34 and input plug 32. Alternatively, in an embodiment not shown, auxiliary receiver 76 may be external to bipolar generator 60 and may collect a sample of control signaling 72 from a coupler or inductive strap (not shown) wrapped around power cord 68. Auxiliary receiver 76 may decode the control signaling 72 and may then direct the decoded output (not shown) into control input 64, thereby avoiding modifications to bipolar generator 60. Optionally, pedal controller 90 (FIGS. 3a and 8) may be plugged into an available control input 64 through pedal control line 98 for providing an additional means for actuating heating current 66.

Referring to FIG. 8, in an embodiment, selective actuation of bipolar generator 60 may be accomplished by an actuator transmitter 74 included in actuating component 40, where a control signaling 72 from control circuit 70 and corresponding to an engagement of switch 36 or lever arm 38 may be wirelessly transmitted to auxiliary receiver 76 external to bipolar generator 60. Auxiliary receiver 76 may then decode control signaling 72 into a suitable format (not shown) for communicating over auxiliary control line 99 into bipolar generator 60 at control input 64. Bipolar generator 60 may then effectuate a desired operational mode of surgical tool 12 based on the decoded output of auxiliary receiver 76. A closed circuit may exist between receptacle 34 and input plug 32. Alternatively, in an embodiment not shown, auxiliary receiver 76 may be internal to bipolar generator 60 for decoding control signaling 72 received wirelessly from actuator transmitter 74. Optionally, pedal controller 90 may be configured to secondarily actuate a cut mode or coagulation mode through pedal control line 98 routed into auxiliary receiver 76 (which is illustrated external to bipolar generator 60) at control input 64a. In an embodiment, auxiliary receiver 76 may combine pedal signaling 96 and control signaling 72 for selectively actuating bipolar generator 60 via auxiliary control line 99.

Referring to FIGS. 7-8, in various embodiments, control signaling 72 may incorporate additional control beyond those effectuating modes of electrosurgery. For example, control signaling may be configured for setting the voltage or duty cycle (not shown) of bipolar generator 60, and may also be configured for setting the operating conditions of other equipment in the operating room (not shown), such as by auxiliary receiver 76 receiving and routing commands directed to equipment other than bipolar generator 60. In other embodiments, actuator assembly 30 may include a microphone and a voice-activated switch for selectively actuating heating current 66.

Referring to FIG. 9, in various embodiments, actuator assembly 30 may include a battery (not shown) for powering control circuit 70 and actuator transmitter 74, the actuator assembly 30 being removed from interposition between tool plug 16 and generator receptacle 28 in order to operate as a remote control and configured for mounting to operating table 100. In an embodiment, upon engagement of lever arm 38, control circuit 70 generates control signaling 72 which is received and decoded by auxiliary receiver 76, selectively actuating bipolar generator 60 through auxiliary control line 99 and control input 64. Upon actuation of bipolar generator 60, heating current 66 is conducted through power cord 68, through the connector pair composed of generator receptacle 28 and tool plug 16, and to the heating end 18 of blades 14 of forceps 12. In an embodiment, pedals 92 and 94 of pedal controller 90 may be depressed to send pedal signaling 96 over pedal control line 98 and into control input 64a for actuating bipolar generator 60.

Continuing with FIGS. 9 and 10, in various embodiments, remote assembly 30 may be handheld, held actuatably in a human mouth, hingedly mounted to a shoe, mounted actuatably to a human upper body, mounted to a positioning arm, and mounted to at least one blade 14 of forceps 12. In an embodiment, actuator assembly 30 may include a blade coupling element (not shown) similar to signaling tap 78 for coupling control signaling 72 of a remote control assembly 30 onto one or both blades 14 of forceps 12. In various embodiments, the actuating component 40 (not shown) may be disposed with a switch (not shown), a lever arm 38, a lever switch mechanism 49 (not shown) integrated into lever arm 38, or a lever arm 38 and switch 36, each permutation for effectuating an electrosurgical mode, such as coagulation. Input plug 32 and output receptacle 34 (not shown) may be excluded from a remote control assembly or their contacts may be insulated.

Referring now to FIGS. 10 and 11, in various embodiments, two elongated conducting members 14 extending from a base end 20 of surgical tool 12 to a heating end 18 may be configured to receive heating current 66 from the bipolar generator 60 through a power cord 68. The bipolar electrosurgical actuating system may include the actuating component of the actuator assembly in an integral configuration with the elongated conducting members. This integral configuration may be built into the base or blades of a bipolar forceps, which may be disposable or reusable or otherwise configured for single use or multiple uses.

There may be no connector intervening between power cord 68 and tool 12. An actuator assembly 30 may be interposed along an available current path 62 extending between a handle 22 of surgical tool 12 and bipolar generator 60, the interposing resulting in, for each conductor interposed, a generator terminal 52 (FIG. 11) conductive to bipolar generator 60 and a tip terminal 54 (FIG. 11) conductive to heating end 18. Actuator assembly 30 may include actuating component 40 having at least one of a switch 36 and a lever arm 38 and being configured to communicate with the bipolar generator 60 to selectively actuate heating current 66 to flow from generator terminal 54 to tip terminal 54 upon engagement of the switch 36 or the lever arm 38, as described for FIGS. 6-8 above. The flow of heating current 66 may be facilitated by at least one of the following actuating steps: closing a hard electrical switch 46 in actuating component 40 (FIG. 6), coupling a control signaling 72 from actuating component 40 onto the available current path 62 and receivable by bipolar generator 60 (FIGS. 7, 10-11), and wirelessly transmitting control signaling 72 from actuating component 40 to and receivable by bipolar generator 60 (FIG. 8).

Continuing with FIGS. 10 and 11, in various embodiments, actuator assembly 30 may be interposed in at least one of the elongated conducting members 14 within a base portion 24 of surgical tool 12 nearer base end 20 (FIG. 10). In an embodiment, switch 36 may comprise a rocker switch for permanent or momentary engagement of an operational mode, such as cauterization (FIG. 10). In embodiments not shown, actuating component 40 may include lever arm 38 extending over the forceps handle 22, as described for FIGS. 3a-3b and 4a-4b above. In another embodiment, actuator assembly 30 may be interposed in power cord 68, and may couple a control signaling 72 from actuating component 40 onto the power cord 68 for receiving by bipolar generator 60 (FIG. 11). Control input 64 may be optionally utilized by a pedal controller 90 (FIG. 3a) for actuating a heating current 66, or may be utilized by auxiliary receiver 76 (which is illustrated external to bipolar generator 60) (FIGS. 8 and 9) for conducting decoded control signaling 72 into bipolar generator 60, thereby selecting an operational mode such as coagulation, cutting, or an off mode.

Referring still to FIGS. 10 and 11, in an embodiment not shown, actuator assembly 30 may interpose power cord 68 where an input plug 32 is added to generator terminal 52 for mating to the power cord and where a blade connector (not shown) is added to tool terminal 54 for clipping or sliding onto forceps blades 14. In this embodiment, tool plug 16 may be bypassed or used strictly for mechanically mounting assembly 30, while heating current 66 may be routed through assembly 30 via the blade connector to blades 14 upon engagement of the switch 36 or the lever arm 38. In another embodiment, assembly 30 may include a jumper cord (functioning as power cord 68) between actuating component 40 and input plug 32, the assembly plugging into a power connector (not shown) mounted on bipolar generator 60 and outputting heating current 66 for delivery to blades 14 via the blade connector described above. In an embodiment, selective actuation may be accomplished by a hard electrical switch closing a circuit between two auxiliary wires (not shown) accompanying the two wires carrying heating current 66, the switch closing for tripping a relay (not shown) actuating the heating current. The relay may be internal to generator 60 or may be included in an auxiliary receiver that generates a pedal signaling 96 for control input 64.

Referring to FIGS. 9 and 10, in various embodiments, insulator 26 may insulatively bind conducting members 14 together, and may allow for their articulation by a surgeon. Additionally, insulator 26 may join power cord 68 with conducting members 14 without the use of connectors. In an embodiment, in FIG. 10, assembly 30 may be interposed on only one conducting member 14 and may acquire access to the second conductor of power cord 68 via a wire (not shown) channeled through member 14 from insulator 26, thereby completing a circuit for sending control signaling 72.

FIGS. 12-22 depict several variations on a particularly advantageous adaption of the structure described thus far that allows a surgeon to precisely maneuver the operative tip or tips of an electrosurgical tool into position for applying an electrical current to target tissues while avoiding the undesired application of electrical current to other areas. The embodiments to be described here enable a surgeon to grip an electrosurgical tool like a pencil with his or her fingers generally pointed toward the target to facilitate precise positioning of the tool. At the same time, it enables actuation of the tool's electrodes with the same hand at the precise time they are in the desired position, while also avoiding inadvertent actuation at other times. And since electrosurgical procedures are often performed at microscopic magnifications, proper coordination between positioning the tool and actuating it is even more important.

Referring to FIGS. 12-15, a first embodiment of a device employing this adaptation of the structure described previously is particularly suited for right-handed operation. It is shown in connection with a bipolar electrosurgical forceps tool 112, depicted in phantom lines in FIG. 12. (Elements in FIGS. 12-22 that find counterparts in the description of previous embodiments are generally identified by the same references with "100" series numbers like those used to describe other features in FIGS. 12-22.) The tool 112 includes two blades 114 similar to those shown in FIGS.

4a-4b, which terminate in heating tips 118. The handle portions 122 are used to maneuver the tool heating tips at a desired surgical location. The handle portions can have serrated gripping surfaces or be perforated (as shown in FIGS. 2 and 4). The tool 112 further includes a tool plug 126 comparable to tool plugs 26 already described. One of the advantages of the actuator assembly 130 to be described is that it can be adapted for use with a wide variety of bipolar electrosurgical tools of standard construction.

An actuator assembly 130 incorporates a switch (not shown; see switch 36 above), which is actuated by a right-hand actuator lever arm 138R in a manner described below. In the present embodiment, the switch is part of an actuating component 140. As in configurations described above, the tool plug 126 includes connector prongs 126a (see prongs 14 above) that mate with receptacles (not shown; see receptacles 34 above) in the actuating component 140. The tool plug 126 also includes an irrigation port 126b to which an irrigation catheter can be connected for irrigating the surgical site during a procedure. This further illustrates the versatility of the actuator assembly in its ability to be used with a wide variety of conventional bipolar surgical tools. Finally, the actuating component 140 includes wiring 142a that connects the switch in the actuating component and the tool tips 118 to control and power circuitry (not shown) consistent with other embodiments described above.

FIG. 15 is an exploded view showing the arrangement of the actuator assembly 130 and the right-hand lever arm 138R to the ends described above. The actuator assembly 130 includes the actuating component 140 with a hinge first part 148a that accepts a hinge second part 148b on a lever arm retaining member 150, which together form a lever arm hinge 148 with an axis of rotation H. The lever arm retaining member includes an opening 152 where the lever arm retaining member transitions from a solid, substantially flat portion proximate the hinge 148 to a hollow, substantially square female mount that accepts a male bayonet-like mounting member 138a at the end of the lever arm 138R. The lever arm retaining member 150 includes a flat-topped circular protuberance 154 extending slightly from the surface of lever arm to engage the switch in the actuator assembly in a fashion described below. In one embodiment the bayonet mount is keyed to the lever arm retaining member to properly orient the lever arm relative to the retaining member and prevent relative rotation of the arm and its retaining member. It will be understood that the subject matter claimed herein encompasses other means of removably connecting the lever arm to the retaining member so that it is keyed to a particular orientation consistent with its intended use, as described further below.

The manner by which the uniquely shaped lever arm 138R facilitates pinpoint placement of the surgical tool while providing more positive control of its actuation can be appreciated by taking FIGS. 12-17 together. For convenience in describing the unique geometry of the lever arm, the drawings define a space using three mutually orthogonal axes, wherein the centerline of the bipolar tool lies generally in the y-z plane. For example, in the embodiment used in this description, the y-z plane is parallel to a longitudinal center line between the tool tips 118 and the prongs 126a on the tool plug 126 (see FIG. 15). The x-y plane is perpendicular to the axis of rotation H of the lever arm about the hinge 148: in the present embodiment the x-axis is also parallel to the direction of movement of the blades when they are squeezed together by the surgeon (arrows A). As shown in the figures, the coordinate system is "right-handed" according to the conventional definition.

The lever arm 138R has a compound curvature in two planes, whereby in a first region proximate to the actuating component 140 it extends obliquely, that is, at an angle to the x-y plane, upward (positive y- and z-directions) for an extent $138R_U$ that curves convex-downward (the negative z-direction) as seen in FIG. 15. It then transitions smoothly to a second region $138R_O$ that extends obliquely upward (positive y- and z-directions) and curves convex-outward (the positive x-direction) as seen in FIG. 15. Finally, the second region $138R_O$ lies substantially in a plane. This configuration enables it to be ergonomically gripped and controlled in at least two different ways depending on the user's preference, as seen in FIGS. 16 and 17. In both cases, a right-handed user will grasp the device with the actuator assembly generally in the palm of his or her hand with the fingers of the hand extending along the right-hand side of the device and with the thumb T on the left-hand side (as viewed in FIG. 12, for example). Depending on the user's preference, he or she can position the first and second fingers of the right hand in at least two positions.

In an "A" position mode of operation, shown in FIG. 16, the first finger is on the handle portion 122 of the right-hand blade, enabling the user to squeeze the tool blades together between the first finger F1 and the thumb T to perform a surgical procedure. When the tool tips are in the desired position, an intermediate portion of the first finger is shifted slightly to exert inward pressure on the lever arm 138R in a region P to rotate the lever arm mounting member so that it pivots counterclockwise about the hinge 148 as indicated by the arrow M in FIG. 13. This moves the switch from a neutral position, into which it is spring-biased and in which the switch is open, to an actuated position in which the switch is closed and current is supplied to the tool tips 18. In a typical construction, movement of the lever arm a small amount (one or two millimeters) will close the switch, so that the slight movement of the first finger F1 required to supply current to the tool tips will not result in any movement of the tool tip at the surgical site.

In a "B" position mode of operation, shown in FIG. 17, the user's thumb T is placed as before, but the second finger F2 is placed on the tool handle portion of the right-hand blade to operate the tool. The first finger F1 is not on the tool itself, but is used only to move the lever arm 138R by pressing on it near its distal end D. It will be appreciated by considering FIGS. 16 and 17 together that ergonomic hand positions are enabled by the lever arm upward curvature from its base toward its distal end (FIG. 13) combined with the outward curvature of the lever arm, designed to match the natural curvature of a user's fingers when the device is grasped, at the region where the lever arm extends along the tool handle portion (FIG. 14).

A cover 180 connected to the actuating component 140 completes the actuator assembly 130 of this embodiment. The cover includes a body portion 182 that attaches to the actuating component in any suitable manner (such as by using an adhesive if the parts are made of a resin material) and a projecting portion 184 that extends from the body portion over the actuating lever arm retaining member 150. As best seen in FIG. 13, the projecting portion forms a guard that prevents the palm of the user's hand from inadvertently rotating the lever arm retaining member 150 and supplying current to the tool tips 118 while the user is manipulating the tool into place (see FIGS. 16 and 17). In an alternate construction, the actuating assembly can interpose a flexible material between the lever arm or lever arm retaining member and the cover's projecting portion to prevent objects from lodging underneath the cover. Such a material can prevent debris from entering the region beneath the cover as well as prevent the risk that a user's finger or hand becomes pinched between the cover and the moving lever arm/lever arm retaining member.

In other variations, the cover can include a surface that has a texture or finish that differs from the feel of the lever arm 138 such that the user can determine via tactile feel that when he or she is touching the cover or the lever arm. In addition, variations of the device can also employ sensors (for example, pressure sensors, touch sensors, optical sensors, etc.) that are in electrical communication with the power supply such that even slight engagement of the cover surface automatically prevents energy delivery even if the lever mounting member engages the switch. A still further variation can use a cover that is removable so that the user has the option of removing it if that would be more suitable for a given procedure.

FIGS. 18-20 depict the actuator assembly of this embodiment mounted to the tool for left-hand operation. Essentially the same parts are used for this configuration, except that the lever arm 138L is specially configured for use with the left hand. FIG. 18 is an isometric view of the device shown in FIG. 12 adapted for left-handed use. The actuator assembly 130 has been detached from the tool plug 126, the tool has been rotated 180°, and then plugged back into the actuator assembly. (Compare FIGS. 13 and 19.) The right-hand lever arm 136R is removed from the lever arm retaining member 150 via the bayonet-like mount (or alternative) and replaced with the left-hand lever arm 138l, which has a similar removable mount. The lever arm 138L also has a compound curvature in two planes, whereby in a first region proximate to the actuating component 140 it extends obliquely upward (positive y- and z-directions) for an extent $138L_U$ that curves convex-downward (the negative z-direction). It then transitions smoothly to a second region $138L_O$ that that extends obliquely upward (positive y- and z-directions) and curves convex-outward (the negative x-direction). Finally, the second region $138L_O$ lies substantially in a plane. Otherwise, like parts and features are described with the same references as used in FIGS. 12-17. The resulting left-hand device is essentially a mirror image of the right-handed device and is operated in the same fashion, as indicated by FIGS. 16 and 17, except for using the left hand instead of the right.

To facilitate conversion between right- and left-hand operation, the lever arms 138R and 138L are provided with distinguishing indicia for identifying their respective handedness, since they are otherwise very similar in appearance on their own. In the present embodiment, each is provided with an orienting tab, indicated by the reference 200R for the lever arm 138R and 200L for the lever arm 138L. In both cases, these orienting tabs are located at the "top" of the lever arm to indicate that the proper orientation of the respective lever arm is with the tab pointing in the plus-z direction. Other orientation indicia can be used instead of, and preferably in combination with, the tabs 200. For example, the right- and left-hand lever arms can have different colors, or color-coded regions.

FIGS. 21-23 depict the actuator assembly of this embodiment with a lever arm 138C that can be used for both left- and right-hand operation. In this variation, a combination lever arm 138C has a first substantially straight region C1 that generally corresponds to the first curved regions $138R_U$ and $138L_U$ of the right- and left-hand lever arms, and a second substantially straight region C2 that that generally corresponds to the second curved regions $138R_U$ and $138L_U$ of the right- and left-hand lever arms. This facilitates conversion between a configuration for right-hand operation (shown in FIGS. 21-23) and a configuration for left-hand operation from the right-hand configuration shown in FIGS. 21-23. This is done simply by detaching the actuator assembly 130 from the tool plug 126, rotating it 180°, and plugging it back into the actuator assembly, as described above in connection with FIGS. 18-20. The lever arm 136C is likewise rotated 180° about an axis along the mounting member 136a (see FIG. 15) and reinserted in the lever arm retaining member 150. The bayonet-like mount (or alternative) is configured to permit insertion of the lever arm 130C in either orientation, and is preferably configured to limit insertion to only those two orientations. The left-hand and right-hand devices are operated in the same fashion described above in connection with FIGS. 12-20.

The foregoing description of the subject matter has been presented for purposes of illustration and description. It is not intended to be exhaustive or to limit the subject matter to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments except insofar as limited by the prior art.

What is claimed is:

1. An actuator assembly adapted for use with a bipolar electrosurgical tool comprising a forceps having a tool plug at a proximal region and two blades mounted to the tool plug with facing interior surfaces, each blade extending from the tool plug to an electrode at a distal region of the blade and having an exterior surface with a handle portion at an intermediate region of the blade for articulation of the forceps by a hand of a user, wherein the tool plug is electrically connected to the electrodes for applying to tissue electrical current introduced to the tool plug as the user articulates the forceps with the handle portions, the actuator assembly comprising:
   a connector for removably mounting the actuator assembly on the tool plug and a switch on the connector movable between an open position and a closed position, the connector being configured for connection to an electrical generating apparatus to introduce the electrical current to the tool plug in response to movement of the switch from the open position to the closed position; and
   an actuator lever arm removably mounted to the connector for rotation about a hinge at a pivot point and positioned for movement of the actuator lever arm by one finger of the user's hand toward the switch to place the switch in the closed position by contacting the switch with the actuator lever arm, wherein:
   a three-dimensional space is defined by a right hand coordinate system having mutually orthogonal x, y, and z axes with a y-z plane parallel to a longitudinal centerline extending generally between the tool plug and the electrodes and an x-y plane perpendicular to an axis of rotation of the actuator lever arm when the actuator assembly is mounted on the tool plug, the y-direction being positive from the tool plug toward the electrodes, and the actuator lever arm includes a first region extending generally in the positive y-direction from the pivot point to a first location, at which the first region connects to a second region curved convex-outward in the x-direction relative to said centerline, said actuator lever arm being spaced from the exterior surface of one of the two blades in the x-direction to permit rotation of the actuator lever arm by the finger of the user toward said exterior surface of said one blade and into contact with the switch when the connector is mounted on the tool plug.

2. The actuator assembly in claim 1, wherein:
the curved second region of the actuator lever arm terminates at a distal end of the lever arm;
the connector includes actuator connecting members for mating with cooperating tool plug connecting members structured for mounting the actuator assembly on the tool plug in at least two different orientations;
when the actuator assembly is mounted on the tool plug in one of said orientations, the second region of the actuator lever arm is curved convex-outward in the positive x-direction for operation by the user's right hand; and
when the actuator assembly is mounted on the tool plug in the other of said orientations, the second region of the actuator lever arm is curved convex-outward in the negative x-direction for operation by the user's left hand.

3. The actuator assembly in claim 2, further comprising a guard for inhibiting inadvertent rotation of the actuator lever arm when the bipolar electrosurgical tool is held in the user's hand.

4. The actuator assembly in claim 3, wherein the guard is removably connected to the connector and extends toward the actuator lever arm in the positive y-direction.

5. The actuator assembly in claim 1, wherein the first region of the actuator lever arm is substantially straight and the actuator lever arm extends obliquely outward in the x-direction relative to said exterior surface of said one blade when the actuator assembly is mounted on the tool plug.

6. The actuator assembly in claim 5, further comprising a guard extending from the connector in the positive y-direction for inhibiting inadvertent rotation of the actuator lever arm when the bipolar electrosurgical tool is held in the user's hand.

7. The actuator assembly in claim 1, further comprising a guard for inhibiting inadvertent rotation of the actuator lever arm when the bipolar electrosurgical tool is held in the user's hand.

8. The actuator assembly in claim 7, wherein the guard is removably connected to the actuator assembly.

9. The actuator assembly in claim 1, wherein the switch comprises a push button switch and rotation of the actuator lever arm in the direction of said exterior surface of said one blade depresses the push button switch into the closed position by contact with the actuator lever arm.

10. The actuator assembly in claim 9, wherein the connector includes an output plug comprising either (i) at least two male connecting members for mating with at least two female sockets of the tool plug, or (ii) at least two female sockets for mating with at least two male connecting members of the tool plug for removably mounting the actuator assembly on the tool plug and electrically connecting each of the at least two male connecting members with a corresponding one of the at least two female sockets.

11. The actuator assembly in claim 1, wherein the connector further includes a power cord for removably connecting the bipolar electrosurgical tool to the electrical generating apparatus.

12. The actuator assembly in claim 2, wherein the actuator connecting members consist of two mating actuator sockets on the connector for accepting two mating tool prongs on the tool plug for mounting the actuator assembly on the bipolar electrosurgical tool and electrically connecting each of the at least two mating prongs with a corresponding one of the at least two mating actuator sockets.

13. The actuator assembly in claim 12, wherein the tool prongs and the actuator sockets lie in the x-y plane when the actuator assembly is mounted on the bipolar electrosurgical tool.

14. The actuator assembly in claim 10, wherein:
the cooperating male connecting members and female connecting sockets are structured for mounting the actuator assembly on the tool plug in at least two different orientations;
when the actuator assembly is mounted on the tool plug in one of said orientations, the second region of the actuator lever arm is curved convex-outward in the positive x-direction for operation by the user's right hand; and
when the actuator assembly is mounted on the tool plug in the other of said orientations, the second region of the actuator lever arm is curved convex-outward in the negative x-direction for operation by the user's left hand.

15. The actuator assembly in claim 14, wherein the connector further includes a power cord for removably connecting the bipolar electrosurgical tool to the electrical generating apparatus.

16. An electrosurgical apparatus comprising:
a bipolar electrosurgical tool comprising a forceps having a tool plug at a proximal region and two blades mounted to the tool plug with facing interior surfaces, each blade extending from the tool plug to an electrode at a distal region of the blade and having an exterior surface with a handle portion at an intermediate region for articulation of the forceps by a hand of a user, wherein the tool plug is electrically connected to the electrodes for applying to tissue electrical current introduced to the tool plug as the user articulates the forceps with the handle portions; and
an actuator assembly at the proximal region of the bipolar electrosurgical tool, the actuator assembly having (i) a connector including a switch movable between an open position and a closed position, (ii) a power cord for removably connecting the apparatus to an electrical generating apparatus to introduce the electrical current to the tool plug when the switch is moved from the open position to the closed position, and (iii) an actuator lever arm removably mounted to the connector for rotation about a hinge at a pivot point and positioned for movement by one finger of the user's hand toward the switch to place the switch in the closed position by contacting the switch with the actuator lever arm, wherein:
a three-dimensional space is defined by a right hand coordinate system having mutually orthogonal x, y, and z axes with a y-z plane parallel to a longitudinal centerline extending generally between the tool plug and the electrodes and an x-y plane perpendicular to an axis of rotation of the actuator lever arm, the y-direction being positive from the tool plug toward the electrodes, and the actuator lever arm includes a first region extending generally in the positive y-direction from the pivot point to a first location, at which the first region connects to a second region curved convex-outward in the x-direction relative to said centerline, said actuator lever arm being spaced from the exterior surface of one of the blades in the x-direction to permit rotation of the actuator lever arm by the finger of the user toward said exterior surface of said one of the two blades and into contact with the switch.

17. The electrosurgical apparatus in claim 16, wherein:

the connector is configured for removably mounting the actuator assembly on the tool plug in one of two different orientations;

when the actuator assembly is mounted on the tool plug in one of said orientations, the second region of the actuator lever arm is curved convex-outward in the positive x-direction for operation by the user's right hand; and when the actuator assembly is mounted on the tool plug in the other of said orientations, the second region of the actuator lever arm is curved convex-outward in the negative x-direction for operation by the user's left hand.

18. The electrosurgical apparatus in claim 16, wherein the actuator assembly further comprises a guard for inhibiting inadvertent rotation of the actuator lever arm by the user.

19. The electrosurgical apparatus in claim 18, wherein the guard is removably connected to the connector.

20. The electrosurgical apparatus in claim 17, wherein the first region of the actuator lever arm is substantially straight and the actuator lever arm extends obliquely outward in the x-direction relative to said exterior surface of said one blade.

* * * * *